(12) United States Patent
Barbas, III et al.

(10) Patent No.: US 6,268,488 B1
(45) Date of Patent: Jul. 31, 2001

(54) PRODRUG ACTIVATION USING CATALYTIC ANTIBODIES

(76) Inventors: Carlos F. Barbas, III, 246 Dolphin Ct., Del Mar, CA (US) 92014; Doron Shabat, 7665 Palmilla Dr., No. 5311, San Diego, CA (US) 92122; Christoph Rader, 4058 Front St., San Diego, CA (US) 92103; Benjamin List, 2116 C St., San Diego, CA (US) 92102; Richard A. Lerner, 7750 Roseland Dr., La Jolla, CA (US) 92037

( * ) Notice: Subject to any disclaimer, the term of this patent is extended or adjusted under 35 U.S.C. 154(b) by 0 days.

(21) Appl. No.: 09/318,661

(22) Filed: May 25, 1999

(51) Int. Cl.[7] .......................... C07H 15/24; C07D 277/30
(52) U.S. Cl. .......................... 536/6.4; 548/204; 549/375; 562/463; 568/448
(58) Field of Search .............................. 514/34, 169, 289, 514/373, 328; 536/6.4; 548/204; 549/375; 562/463; 568/448

(56) References Cited

U.S. PATENT DOCUMENTS 5,001,115 * 3/1991 Sloan ..................................... 514/34

OTHER PUBLICATIONS

Senter, et al., "Anti–tumor Effects on Antibody–Alkaline Phosphatase Conjugates in Combination with Etoposide Phosphate", *Proc. Natl. Acad. Sci. USA* 85: 4842–4846 (1988).

Bagshawe, et al., "A Cytotoxic Agent can be Generated Selectively at Cancer Sites", *Br. J. Cancer* 58: 700–703 (1988).

Miyashita, et al., "Prodrug Activation via Catalytic Antibodies", *Proc. Natl. Acad. Sci. USA* 90: 5337–5340 (1993).

Campbell, et al., "Antibody–Catalyzed Prodrug Activation", *J. Am. Chem. Soc.* 116: 2165–2166 (1994).

Wentworth, et al., "Toward Antibody–Directed "Abzyme" Prodrug Therapy, ADAPT: Carbamate Prodrug Activation by a Catalytic Antibody and its in vitro Application to Human Tumor Cell Killing", *Proc. Natl. Acad. Sci. USA* 93: 799–803 (1996).

Niculescu–Duvaz, et al., "Antibody–Directed Enzyme Prodrug Therapy (ADEPT): A Review", *Adv. Drug. Del. Rev.* 26: 151–172 (1997).

Denmeade, et al., "Enzyme Activation of a Doxorubicin–Peptide Prodrug by Prostate–Specific Antigen", *Cancer Res.* 58: 2537–2540 (1998).

List, et al., "Aldol Sensors for the Rapid Generation of Tunable Fluorescence by Antibody Catalysis", *Proc. Natl. Acad. Sci. USA* 95: 15351–15355 (1998).

* cited by examiner

*Primary Examiner*—Elli Peselev
(74) *Attorney, Agent, or Firm*—Thomas E. Northrup

(57) ABSTRACT

The present invention provides a compound that includes an active therapeutic agent attached to a blocking moiety that is sensitive to the catalytic action of molecules having retroaldol and retro-Michael catalytic activity, methods for making such compounds and methods of converting such compounds to active therapeutic agents using molecules having aldolase activity.

15 Claims, 12 Drawing Sheets

```
            10              20              30              40
GGT TTC GCT ACC GTT GCT CAG GCT GCT CAC CAT CAC CAC CAC CAT
CCA AAG CGA TGG CAA CGA GTC CGA CGA GTG GTA GTG GTG GTG GTA
 G   F   A   T   V   A   Q   A   A   H   H   H   H   H   H>

50              60              70              80              90
GTG GCC CAG GCG GCC AGT TCC GAG CTC GAC ATT GTG ATG ACC CAG
CAC CGG GTC CGC CGG TCA AGG CTC GAG CTG TAA CAC TAC TGG GTC
 V   A   Q   A   A   S   S   E   L   D   I   V   M   T   Q>

100             110             120             130
TCT CCA CTC TCC CTG CCT GTC CGT CTT GGA GAT CAA GCC TCC ATC
AGA GGT GAG AGG GAC GGA CAG GCA GAA CCT CTA GTT CGG AGG TAG
 S   P   L   S   L   P   V   R   L   G   D   Q   A   S   I>

140             150             160             170             180
TCT TGC AGA TCT AGT CAG AGC CTT CTA CAC ACT TAT GGA AGC CCC
AGA ACG TCT AGA TCA GTC TCG GAA GAT GTG TGA ATA CCT TCG GGG
 S   C   R   S   S   Q   S   L   L   H   T   Y   G   S   P>

190             200             210             220
TAT TTA AAT TGG TAC CTG CAG AAG CCA GGC CAG TCG CCA AAG CTC
ATA AAT TTA ACC ATG GAC GTC TTC GGT CCG GTC AGC GGT TTC GAG
 Y   L   N   W   Y   L   Q   K   P   G   Q   S   P   K   L>

230             240             250             260             270
CTG ATC TAC AAA GTT TCC AAC CGC TTT TCT GGG GTC CCA GAC AGG
GAC TAG ATG TTT CAA AGG TTG GCG AAA AGA CCC CAG GGT CTG TCC
 L   I   Y   K   V   S   N   R   F   S   G   V   P   D   R>

280             290             300             310
TTC AGT GGC AGT GGA TCA GGG ACA GAT TTC ACA CTC AGG ATC AGC
AAG TCA CCG TCA CCT AGT CCC TGT CTA AAG TGT GAG TCC TAG TCG
 F   S   G   S   G   S   G   T   D   F   T   L   R   I   S>

320             330             340             350             360
AAA GTG GAG GCT GAG GAT CTG GGA GTT TAT TTC TGC TCT CAA GGT
TTT CAC CTC CGA CTC CTA GAC CCT CAA ATA AAG ACG AGA GTT CCA
 K   V   E   A   E   D   L   G   V   Y   F   C   S   Q   G>

370             380             390             400
ACA CAT CTT CCG TAC ACG TTC GGA GGG GGG ACC AAG CTG GAA ATA
TGT GTA GAA GGC ATG TGC AAG CCT CCC CCC TGG TTC GAC CTT TAT
 T   H   L   P   Y   T   F   G   G   G   T   K   L   E   I>

410             420             430             440             450
AAA TCC TCT GGT GGC GGT GGC TCG GGC GGT GGT GGG GGT GGT TCC
TTT AGG AGA CCA CCG CCA CCG AGC CCG CCA CCA CCC CCA CCA AGG
 K   S   S   G   G   G   G   S   G   G   G   G   G   G   S>

460             470             480             490
TCT AGA TCT TCC CTC GAG GTG ATG TTG GTG GAG TCT GGA GGA GGC
AGA TCT AGA AGG GAG CTC CAC TAC AAC CAC CTC AGA CCT CCT CCG
 S   R   S   S   L   E   V   M   L   V   E   S   G   G   G>

500             510             520             530             540
TTG GTG CAA CCT GGA GGA ACC ATG AAA CTC TCC TGT GAA ATT TCT
AAC CAC GTT GGA CCT CCT TGG TAC TTT GAG AGG ACA CTT TAA AGA
 L   V   Q   P   G   G   T   M   K   L   S   C   E   I   S>
```

FIG. 9A

```
             550            560           570            580
GGA TTA ACT TTC AGA AAT TAT TGG ATG TCT TGG GTC CGC CAG TCT
CCT AAT TGA AAG TCT TTA ATA ACC TAC AGA ACC CAG GCG GTC AGA
 G   L   T   F   R   N   Y   W   M   S   W   V   R   Q   S>

590           600            610            620          630
CCA GAG AAG GGG CTT GAG TGG GTT GCT GAA ATT AGA TTG AGA TCT
GGT CTC TTC CCC GAA CTC ACC CAA CGA CTT TAA TCT AAC TCT AGA
 P   E   K   G   L   E   W   V   A   E   I   R   L   R   S>

640            650           660            670
GAT AAT TAT GCA ACA CAT TAT GCG GAG TCT GTG AAA GGG AAG TTC
CTA TTA ATA CGT TGT GTA ATA CGC CTC AGA CAC TTT CCC TTC AAG
 D   N   Y   A   T   H   Y   A   E   S   V   K   G   K   F>

680            690           700            710          720
ACC ATC TCA AGA GAT GAT TCC AAA AGT CGT CTC TAC CTG CAA ATG
TGG TAG AGT TCT CTA CTA AGG TTT TCA GCA GAG ATG GAC GTT TAC
 T   I   S   R   D   D   S   K   S   R   L   Y   L   Q   M>

730            740           750            760
AAC AGC TTA AGA ACT GAA GAC ACT GGA ATT TAT TAC TGT AAA ACC
TTG TCG AAT TCT TGA CTT CTG TGA CCT TAA ATA ATG ACA TTT TGG
 N   S   L   R   T   E   D   T   G   I   Y   Y   C   K   T>

770            780           790            800          810
TAT TTT TAC TCA TTT TCT TAC TGG GGC CAA GGG ACT CTG GTC ACT
ATA AAA ATG AGT AAA AGA ATG ACC CCG GTT CCC TGA GAC CAG TGA
 Y   F   Y   S   F   S   Y   W   G   Q   G   T   L   V   T>

820            830           840            850
GTC TCT GCA GCC TCC ACA CAG AGC CCA TCC GTC ACT AGT GGC CAG
CAG AGA CGT CGG AGG TGT GTC TCG GGT AGG CAG TGA TCA CCG GTC
 V   S   A   A   S   T   Q   S   P   S   V   T   S   G   Q>

860           870            880            890
GCC GGC CAG TAC CCG TAC GAC GTT CCG GAC TAC GCT TCT TAA AA
CGG CCG GTC ATG GGC ATG CTG CAA GGC CTG ATG CGA AGA ATT TT
 A   G   Q   Y   P   Y   D   V   P   D   Y   A   S   *   X>
```

FIG. 9B

```
                10                  20                  30                  40
GCT ACC GTT GCT CAG GCT GCT CAC CAT CAC CAT CAC CAT GTG GCC
CGA TGG CAA CGA GTC CGA CGA GTG GTA GTG GTA GTG GTA CAC CGG
 A   T   V   A   Q   A   A   H   H   H   H   H   H   V   A>

50                  60                  70                  80                  90
CAG GCG GCC AGT TCC GAG CTC GAT GTT GTG ATG ACC CAG ACT CCA
GTC CGC CGG TCA AGG CTC GAG CTA CAA CAC TAC TGG GTC TGA GGT
 Q   A   A   S   S   E   L   D   V   V   M   T   Q   T   P>

100                 110                 120                 130
CTC TCC CTG CCT GTC AGT CTT GGA GAT CAA GCC TCC ATC TCT TGC
GAG AGG GAC GGA CAG TCA GAA CCT CTA GTT CGG AGG TAG AGA ACG
 L   S   L   P   V   S   L   G   D   Q   A   S   I   S   C>

140                 150                 160                 170                 180
AGA TCT AGT CAG AGC CTT GTA CAC AGT TAT GGA AAC ACC TTT TTA
TCT AGA TCA GTC TCG GAA CAT GTG TCA ATA CCT TTG TGG AAA AAT
 R   S   S   Q   S   L   V   H   S   Y   G   N   T   F   L>

190                 200                 210                 220
AAT TGG TAC CTG CAG AAG TCA GGC CAG TCT CCA AAG CTC CTG ATC
TTA ACC ATG GAC GTC TTC AGT CCG GTC AGA GGT TTC GAG GAC TAG
 N   W   Y   L   Q   K   S   G   Q   S   P   K   L   L   I>

230                 240                 250                 260                 270
TAC AAA GTT TCC AAC CGA TTT TCT GGG GTC CCA GAC AGG TTC AGT
ATG TTT CAA AGG TTG GCT AAA AGA CCC CAG GGT CTG TCC AAG TCA
 Y   K   V   S   N   R   F   S   G   V   P   D   R   F   S>

280                 290                 300                 310
GGC AGT GGA TCA GGG ACA GAT TTC ACA CTC AAG ATC AGC AGA GTG
CCG TCA CCT AGT CCC TGT CTA AAG TGT GAG TTC TAG TCG TCT CAC
 G   S   G   S   G   T   D   F   T   L   K   I   S   R   V>

320                 330                 340                 350                 360
GAG GCT GAG GAT CTG GGA GTT TAT TTC TGC TCT CAA GGT ACA CAT
CTC CGA CTC CTA GAC CCT CAA ATA AAG ACG AGA GTT CCA TGT GTA
 E   A   E   D   L   G   V   Y   F   C   S   Q   G   T   H>

370                 380                 390                 400
GTT CCG TAC ACG TTC GGA GGG GGG ACC AAG CTG GAG CTG AAA TCC
CAA GGC ATG TGC AAG CCT CCC CCC TGG TTC GAC CTC GAC TTT AGG
 V   P   Y   T   F   G   G   G   T   K   L   E   L   K   S>

410                 420                 430                 440                 450
TCT GGT GGC GGT GGC TCG GGC GGT GGT GGG GGT GGT TCC TCT AGA
AGA CCA CCG CCA CCG AGC CCG CCA CCA CCC CCA CCA AGG AGA TCT
 S   G   G   G   G   S   G   G   G   G   G   S   S   R>

460                 470                 480                 490
TCT TCC CTC GAG GTG ATG CTG GTG GAG TCT GGA GGA GGC TTG GTG
AGA AGG GAG CTC CAC TAC GAC CAC CTC AGA CCT CCT CCG AAC CAC
 S   S   L   E   V   M   L   V   E   S   G   G   G   L   V>

500                 510                 520                 530                 540
CAA CCT GGA GGA TCC ATG AAA CTC TCC TGT GTG GTG TCT GGA TTA
GTT GGA CCT CCT AGG TAC TTT GAG AGG ACA CAC CAC AGA CCT AAT
 Q   P   G   G   S   M   K   L   S   C   V   V   S   G   L>
```

FIG. 10A

```
             550           560           570           580
ACC TTC AGT AGA TTC TGG ATG TCT TGG GTC CGC CAG TCT CCA GAG
TGG AAG TCA TCT AAG ACC TAC AGA ACC CAG GCG GTC AGA GGT CTC
 T   F   S   R   F   W   M   S   W   V   R   Q   S   P   E>

590           600           610           620           630
AAG GGG CTT GAG TGG GTT GCT GAA ATT AGA TTG AAA TCT GAT AAT
TTC CCC GAA CTC ACC CAA CGA CTT TAA TCT AAC TTT AGA CTA TTA
 K   G   L   E   W   V   A   E   I   R   L   K   S   D   N>

640           650           660           670
TAT GCA ACA CAT TAT GCG GAG TCT GTG AAA GGG AAG TTC ACC ATC
ATA CGT TGT GTA ATA CGC CTC AGA CAC TTT CCC TTC AAG TGG TAG
 Y   A   T   H   Y   A   E   S   V   K   G   K   F   T   I>

680           690           700           710           720
TCA AGA GAT GAT TCC AAA AGT CGT CTC TAC CTG CAA ATG AAC AGC
AGT TCT CTA CTA AGG TTT TCA GCA GAG ATG GAC GTT TAC TTG TCG
 S   R   D   D   S   K   S   R   L   Y   L   Q   M   N   S>

730           740           750           760
TTA AGA ACT GAA GAC ACT GGA ATT TAT TAC TGT AAA ATC TAT TTT
AAT TCT TGA CTT CTG TGA CCT TAA ATA ATG ACA TTT TAG ATA AAA
 L   R   T   E   D   T   G   I   Y   Y   C   K   I   Y   F>

770           780           790           800           810
TAC TCT TTT TCT TAC TGG GGC CAA GGG ACT CTG GTC ACT GTC TCT
ATG AGA AAA AGA ATG ACC CCG GTT CCC TGA GAC CAG TGA CAG AGA
 Y   S   F   S   Y   W   G   Q   G   T   L   V   T   V   S>

820           830           840           850
GCA GCC TCC ACA CAG AGC CCA TCC GTC ACT AGT GGC CAG GCC GGC
CGT CGG AGG TGT GTC TCG GGT AGG CAG TGA TCA CCG GTC CGG CCG
 A   A   S   T   Q   S   P   S   V   T   S   G   Q   A   G>

PRODRUG ACTIVATION USING CATALYTIC ANTIBODIES

Funds supporting some of the studies reported herein came from the National Institutes of Health (CA27489). The United States Government may therefore have certain rights in this invention.

TECHNICAL FIELD OF THE INVENTION

The field of this invention is prodrug activation. More particularly, the present invention pertains to a compound that includes an active therapeutic agent attached to a blocking group, methods for making such compounds and methods of converting such compounds to active therapeutic agents using antibodies having aldolase activity.

BACKGROUND OF THE INVENTION

Drug therapy can be limited by nonspecific toxicity. To overcome this limitation, several approaches towards a site-selective therapy have been suggested. Selective therapy can be based on the enzymatic activation of a prodrug at a target site. Unless the target displays a specific enzymatic activity that can be used for prodrug activation (Denmeade et al., Cancer Res 58, 2537–2540, 1998), the enzymatic activity has to be conjugated to an antibody that binds to a target cell surface antigen selectively expressed at the target site. The antibody-enzyme conjugate is injected first. Once it has accumulated at the site and has been cleared from the periphery, the prodrug is administered. The prodrug is selectively activated by the targeted enzymatic activity. One molecule of enzyme catalyzes the activation of many molecules of prodrug. This inherent amplification feature of the system allows the generation of high drug concentrations at the target site. The concept of antibody-directed enzyme prodrug therapy, termed ADEPT, has been developed by Bagshawe, Senter, and others (Bagshawe et al., Br. J. Cancer 58, 700–703, 1988; Senter et al., Proc. Natl. Acad. Sci. USA 85, 4842–4846, 1988; Niculescu-Duvaz, et al., Adv. Drug Delivery Rev. 26, 151–172, 1997). A number of antigens that are expressed on the surface of cells have been shown to be effective targets for antibody-mediated therapy. Thus, the antibody component is not the critical parameter for ADEPT. By contrast, the requirements for the enzyme component for ADEPT are difficult to achieve. First of all, selective prodrug activation requires the catalysis of a reaction that must not be accomplished by endogenous enzymes in blood and normal tissue of the patient. Enzymes of non-mammalian origin that meet these needs are, however, likely to be highly immunogenic, a fact that makes repeated administration impossible. There is a need in the art, therefore, for improved ADEPT compounds and methods.

BRIEF SUMMARY OF THE INVENTION

In one aspect, the present invention provides a compound according to formula I, below

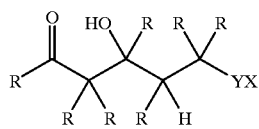

In formula I, X is a heteroatom of a target molecule and Y is absent or a self-immolative linker such as shown below:

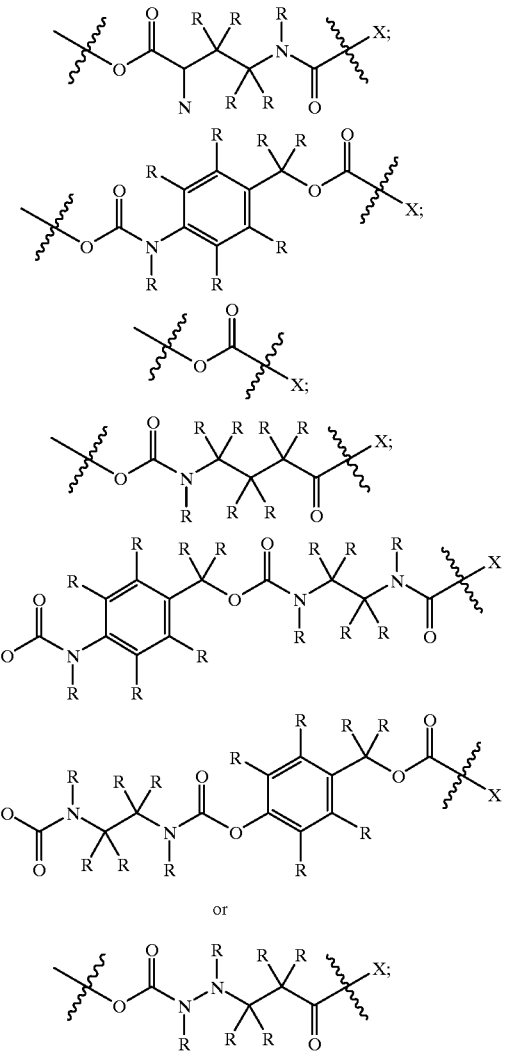

Each R is independently hydrogen, $C_1$–$C_6$ alkyl, $C_1$–$C_6$ alkenyl, $C_5$–$C_6$ aryl or a heterocycle containing five or six ring atoms. In one embodiment, the heteroatom is a nitrogen, oxygen or sulfur atom in a functional group of the target molecule. Preferred target molecules are therapeutic agents or fluorescent molecules. Exemplary and preferred therapeutic agents include anti-tumor agents such as a cytotoxic agent, a microtubule stabilizing agent or an antibiotic. A preferred antibiotic is an anthracycline antibiotic such as doxorubicin or a therapeutically active analog thereof. A preferred microtubule stabilizing agent is paclitaxel, epothilone, or a therapeutically active analog thereof.

In another aspect, a compound of the present invention includes a compound having the structure II, below

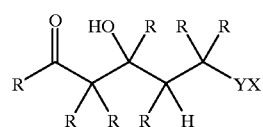

where X, Y and R are defined in reference to formula I.

An especially preferred compound of this invention has the structure

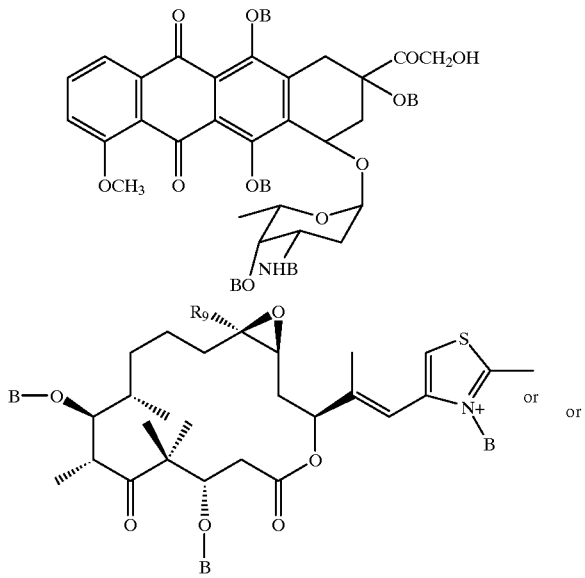

where $R^9$ is $CH_3$, $CH_2F$, $CH_2Cl$, $CH_2CH_3$, $CH_2OOCCH_3$ or $CH=CH_2$ and each B is independently H,

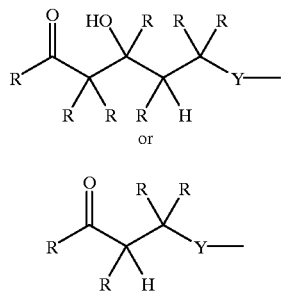

where Y and R are as defined above and with the proviso that two Bs are H.

In another aspect, this invention provides a of converting an inactive molecule to an active molecule. The process includes the step of exposing the inactive molecule to an agent that catalyzes a retro-Michael reaction. A preferred inactive molecule is a compound according to formula I or II, above. A preferred agent that catalyzes a retro-Michael reaction is a protein. A preferred is an antibody, the catalytic activity of which is inhibited by a β-diketone compound. Exemplary and preferred such antibodies are 38C2 or 33F12. The process can occur in vitro, in situ or in vivo. In one embodiment, the antibody is a bifunctional antibody that specifically immunoreacts with a cell surface antigen of a target cell such as a tumor cell or a virus-infected cell. The antibody can be a single chain antibody.

BRIEF DESCRIPTION OF THE DRAWINGS

In the drawings that form a portion of the specification

FIG. 9 gives the top strand nucleotide (SEQ ID NO:1) and bottom strand (SEQ ID NO 5) and amino acid residue (SEQ ID NO:2) sequence of the catalytic fragment of antibody 38C2.

FIG. 10 gives the top strand nucleotide (SEQ ID NO:3) and bottom strand (SEQ ID NO 6) and amino acid residue (SEQ ID NO:4) sequence of the catalytic fragment of antibody 33F12.

DETAILED DESCRIPTION OF THE INVENTION

Figure 1:
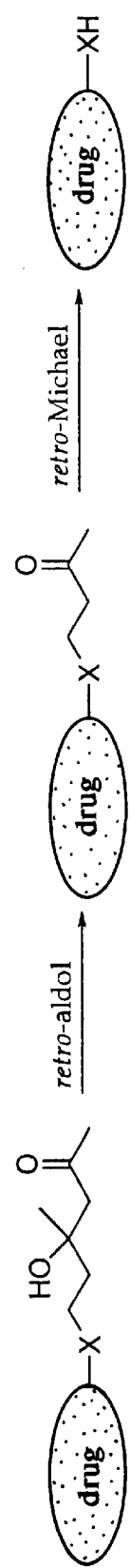
FIG. 1 shows prodrug activation via a tandem retro-aldol-retro-Michael reaction. X stands for heteroatoms N, O, or S.

The following is a list of some of the definitions used in the present disclosure.

An "alkyl" group refers to a saturated aliphatic hydrocarbon, including straight-chain, branched-chain, and cyclic alkyl groups. The alkyl group may have 1 to 12 carbons, or may have 3 to 9 carbons. The alkyl group may be substituted or unsubstituted. When substituted, the substituted groups may be hydroxyl, halogen, cyano, alkoxy, =O, =S, $NO_2$ or $N(CH_3)_2$, amino, SH, or aryl.

An "alkenyl" group refers to an unsaturated hydrocarbon group containing at least one carbon-carbon double bond, including straight-chain, branched-chain, and cyclic groups. The alkenyl group may have 2 to 12 carbons, or may have 3 to 9 carbons. The alkenyl group may be substituted or unsubstituted. When substituted, the substituted groups may be hydroxyl, halogen, cyano, alkoxy, =O, =S, $NO_2$ or $N(CH_3)_2$, amino, SH, or aryl.

An "alkynyl" group refers to an unsaturated hydrocarbon group containing at least one carbon-carbon triple bond, including straight-chain, branched-chain, and cyclic groups. The alkynyl group may have 2 to 12 carbons, or may have 3 to 9 carbons. The alkynyl group may be substituted or unsubstituted. When substituted the substituted groups may be, hydroxyl, halogen, cyano, alkoxy, =O, =S, $NO_2$ or $N(CH_3)_2$, amino, SH, or aryl.

An "alkoxy" group refers to an "—O-alkyl" group, where "alkyl" is defined as described above.

An "aryl" group refers to an aromatic group which has at least one ring having conjugated pi electron system and includes carbocyclic aryl, heterocyclic aryl and biaryl groups, all of which may be optionally substituted. The substituents of the aryl groups may be hydroxyl, halogen, cyano, alkoxy, alkyl, alkenyl, alkynyl, amino, or aryl groups.

An alkylaryl group refers to an alkyl (as described above) covalently bonded to an aryl group (as described above).

Heterocyclic aryl groups are groups having from 1 to 3 heteroatoms as ring atoms in the aromatic ring and the remainder of the ring atoms are carbon atoms. Suitable heteroatoms may include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted.

Heterocyclic aryl groups are groups having from 1 to 3 heteroatoms as ring atoms in the aromatic ring and the remainder of the ring atoms are carbon atoms. Heteroatoms may include oxygen, sulfur, and nitrogen, and include furanyl, thienyl, pyridyl, pyrrolyl, N-lower alkyl, pyrrolo, pyrimidyl, pyrazinyl, imidazolyl and the like, all optionally substituted.

An "amine" refers to a —N(R'')R''', where R'' and R''', may be independently hydrogen, alkyl, aryl, or alkylaryl.

A "thioamide" refers to —C(S)—NR'R''', where R'' and R''' are as defined above.

I. The Invention

The present invention provides a compound that includes an active therapeutic agent attached to a blocking moiety that is sensitive to the catalytic action of molecules having retro-aldol and retro-Michael catalytic activity, methods for making such compounds and methods of converting such compounds to active therapeutic agents using molecules having aldolase activity.

II. Compounds

A compound of this invention includes a molecule linked to a blocking moiety in such a manner that the activity of the molecule is inhibited or blocked. Any molecule capable of being linked to the blocking group can be used in the compound. Thus, the molecule can include polypeptides, carbohydrates and lipids or any combination thereof. All that is required is that the molecule contains a reactive heteroatom (e.g., nitrogen, oxygen or sulfur) within a functional group of the molecule. Suitable functional groups include alcohols, amines (primary, secondary and tertiary), thiols, thiolamines, and heterocycles. Especially preferred molecules are chromophores, fluorophores and therapeutic agents (e.g., drugs).

The blocking moiety linked to the molecule is characterized as being cleavable by an agent that catalyzes a retro-Michael reaction. Retro-Michael reactions and catalysts for such reactions are well known in the art. A schematic illustration of a retro-Michael reaction is shown below.

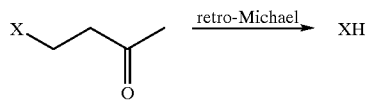

The blocking moiety can contain numerous structures that are subject to retro-Michael cleavage. In addition, the blocking moiety can include structures that are subject to cleavage in a retro-aldol reaction, which reaction is schematically shown below.

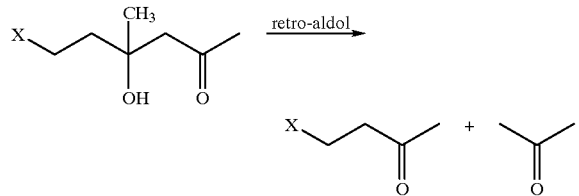

One of skill in the art will recognize that combinations of structures subject to cleavage via retro-Michael and retro-aldol reactions can also be used in a blocking moiety of this invention.

In one aspect, therefore, the present invention provides a compound of formula I, below.

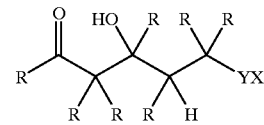

In formula I, X is a heteroatom of a target molecule and Y is absent, a self-immolative linker,

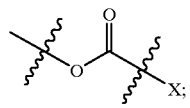

-continued

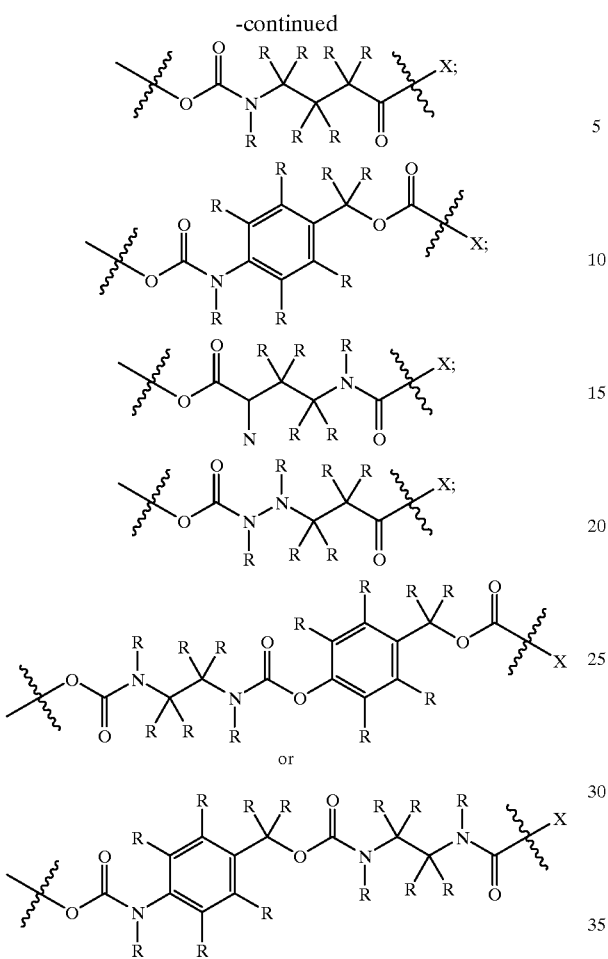

Each R is independently hydrogen, $C_1$–$C_6$ alkyl $C_1$–$C_6$ alkenyl, $C_5$–$C_6$ aryl or a heterocycle containing five or six ring atoms. R can be substituted or unsubstituted, saturated or unsaturated as defined above.

Preferably, the heteroatom, X, is a nitrogen (N), oxygen (O), or sulfur (S) atom. The heteroatom is situated in a reactive, functional group of the molecule. Exemplary such functional groups include alcohols, amines, thiols, thiolamines, heterocycles and the like. Any molecule can be included in a compound of the present invention. The molecule can include peptide, carbohydrate and/or lipid structures. Preferred molecules included in a compound of this invention include chromophores, fluorophores and therapeutic agents. When linked to a blocking moiety, such molecules are inactive. That is, they do not emit light or possess therapeutic activity. Steroid and peptide hormones are exemplary therapeutic agents. An especially preferred therapeutic agent is an anti-tumor drug. Anti-tumor drugs are well known in the art (See, e.g., Physicians Desk Reference).

In one embodiment, the anti-tumor agent is a cytotoxic agent that works by killing tumor cells. One class of anti-tumor, cytotoxic agents is antibodies. An exemplary and preferred such antibiotic is an anthracycline antibiotic (e.g., doxorubicin). Therapeutically active analogs of doxorubicin can also be used. Such analogs are well known in the art (See, e.g., U.S. Pat. Nos. 5,625,043; 5,348,946; 4,826,964; PCT Publication WO97/19954; PCT Publication WO97/

34612, the disclosures of which are incorporated herein by reference). An exemplary doxorubicin compound of this invention is set forth below.

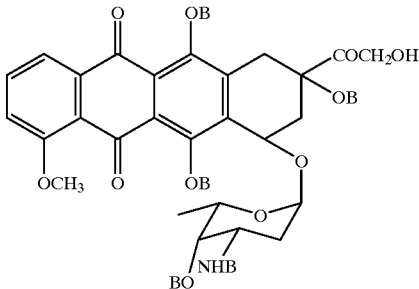

Each B is independently H or a blocking moiety as set forth above. Exemplary blocking moieties have the structure

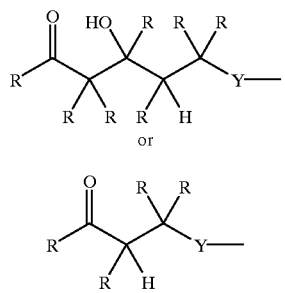

where Y and R are as defined above. Preferably only one B is a blocking moiety (e.g., two Bs are H). The use of doxorubicin to prepare a compound of this invention is set forth hereinafter in the Examples.

In another embodiment, the anti-tumor, cytotoxic agent is a microtubule stabilizing agent. Exemplary and preferred such microtubule stabilizing agents are paclitaxel, epothilone, and therapeutically analogs thereof. Epothilone A and epothilone B are natural substances isolated from myxobacteria Sorangium cellulosum strain 90. These natural substances exhibit cytotoxicity against taxol-resistant tumor cells and may prove to have a clinical utility comparable or superior to paclitaxel [Horwitz et al., Nature 277, 665–667 (1979); Nicolaou et al. Angew. Chem. Int. Ed. Engl. 33, 15–44 (1994)]. Like paclitaxel, the epothilones are thought to exert their cytotoxicity by induction of microtubule assembly and stabilization. [Bollag et al., Cancer Res. 55, 2325–2333 (1995); Kowalski et al., J. Biol. Chem. 272, 2534–2541 (1997)]. Epothilones are reported to be about 2000–5000 times more potent than paclitaxel with respect to the stabilization of microtubules. Despite the marked structural differences between the epothilones and paclitaxel, the epothilones were found to bind to the same region on microtubules and to displace paclitaxel from its binding site. Numerous therapeutic analogs of epothilone have been described (See, e.g., PCT Publication No. WO/96/xxxx, the disclosure of which is incorporated herein by reference). In one embodiment, an epothilone derivative of the structure below can be used in a compound of this invention.

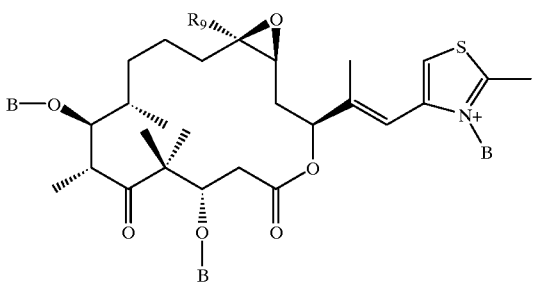

$R^9$ is $CH_3$, $CH_2F$, $CH_2Cl$, $CH_2CH_3$, $CH_2OOCCH_3$ or $CH=CH_2$ and B is a blocking moiety as set forth above.

The present invention further provides a pharmaceutical composition. The pharmaceutical composition includes a compound of this invention together with a physiologically tolerable carrier. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-aminoethanol, histidine, procaine and the like. Particularly preferred are the salts of TFA and HCl.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains a therapeutically effective amount of compound of the present invention, typically formulated to contain an amount of at least 0.1 weight percent of compound per weight of total therapeutic composition. A weight percent is a ratio by weight of inhibitor to total composition. Thus, for example, 0.1 weight percent is 0.1 grams of inhibitor per 100 grams of total composition.

A compound of this invention can be made using standard procedures well known in the art. A particular therapeutic agent is reacted with a blocking moiety attached to a leaving group under suitable conditions and for a period of time sufficient for formation of the compound. The blocking moiety structure is set forth above. Leaving groups are well known in the art. Exemplary leaving groups are activated esters such aspara-nitrophenol and carbamoyl halides such as carbamoyl chloride. The blocking moiety is linked to the leaving group using standard procedures well known in the art. The preparation of a compound of the present invention containing the anti-tumor agent, doxorubicin, is set forth hereinafter in the Examples.

Where the therapeutic agent contains more than one heteroatom in multiple functional groups it may be necessary to prevent those functional groups and heteroatoms from reacting with the blocking moiety. This can be accomplished with the use of N, O or S protecting groups. Such groups are well known in the art.

3. Process of Converting a Blocked Molecule to an Active Molecule

As set forth above, a compound of the present invention includes a molecule attached to a blocking moiety that inactivates the molecule. By way of example, a compound of this invention can be a prodrug. A prodrug of this invention can be converted to a drug (i.e., the active therapeutic agent) by removing the blocking moiety from the compound. Such prodrug activation is based on cleavage of the blocking moiety off the molecule. The present invention, therefore, also provides a process of converting a compound of this invention to an active molecule. In accordance with the process, a compound as set forth above is reacted with an agent that catalyzes the retro-aldol reaction under conditions and for a period of time suitable for formation of the active therapeutic agent.

Any agent that catalyzes the reaction can be used. In one embodiment, the molecule is a protein. A preferred protein is an antibody or catalytically active fragment thereof (collectively referred to herein as an "antibody"). Antibodies having selective catalytic activity are well known in the art. Preferred antibodies are those whose catalytic activity is inhibited by compounds that contain a β-diketone structure. Exemplary and preferred such antibodies are antibodies 38C2 and 33F12. 38C2 is particularly preferred. Catalytic antibody 38C2 was generated using the process of reactive immunization by which the enamine mechanism of natural aldolases was imprinted within the antibody binding site (Wagner et al., *Science* 270, 1797–1800, 1995). Through a reactive lysine buried in a hydrophobic pocket at the base of the substrate binding site, 38C2 catalyses aldol and retro-aldol reactions at a rate comparable to reactions catalyzed by natural enzymes (Barbas et al., *Science* 278, 2085–2092, 1997). Unlike its natural enzyme counterparts, however, 38C2 accepts a wide variety of substrates (Barbas et al., *Science* 278, 2085–2092, 1997; Hoffmann et al., *J. Am.*

Chem. Soc. 120, 2768–2779, 1998). This feature has been exploited in enantioselective organic synthesis (e.g., List et al., Chem. Eur. J. 4, 881–885, 1998a) and makes 38C2 an ideal candidate for prodrug activation. The broad scope of 38C2 bears the potential for the activation of a number of structurally distinct prodrugs, which might be of advantage not only for the treatment of a wider range of tumors but also the repeated treatment of tumors that develop resistance to certain drugs.

Figure 3:
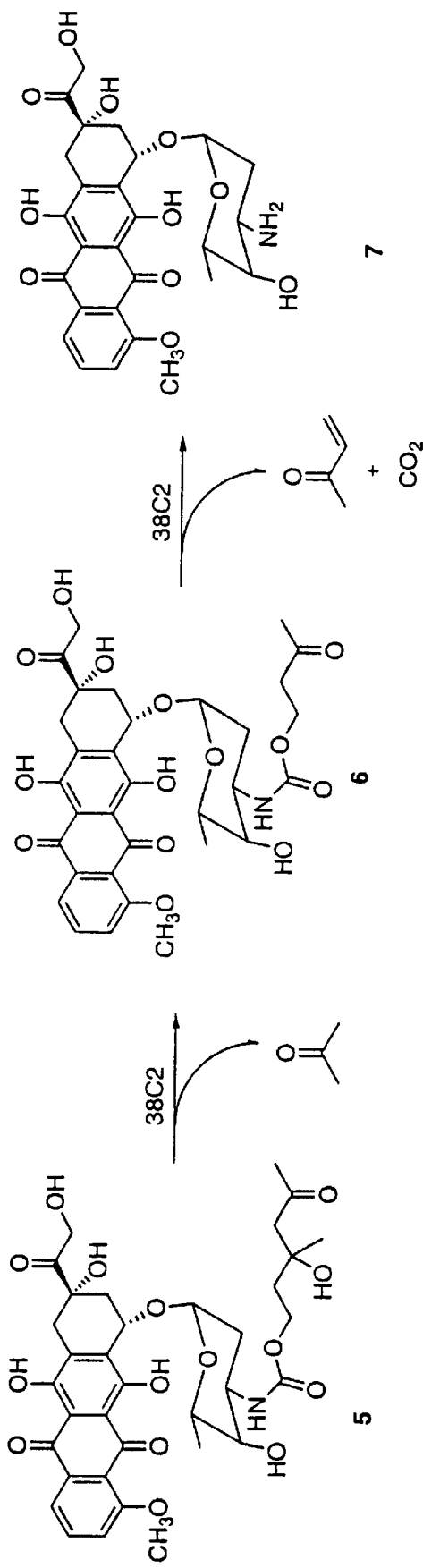
FIG. 3 shows doxorubicin prodrug activation via a tandem retro-aldol-retro-Michael reaction catalyzed by antibody 38C2.

The use of 38C2 to convert pro-doxorubicin to doxorubicin is schematically shown in FIG. 3. First, the antibody-catalyzed retro-aldol reaction of pro-doxorubicin gives ketone and acetone. The second step consists of antibody-catalyzed retro-Michael reaction, release of methyl vinyl ketone, carbon dioxide and the free doxorubicin. Since both reactions are catalyzed by the antibody, one may wonder why not use only the retro-Michael reaction that actually leads to the free drug release. The reason for that is the relative high background of this reaction at physiological pH. By coupling the retro-aldol reaction to retro-Michael reaction the background reaction is almost eliminated and consequently prevented prodrug activation without the antibody.

In one embodiment, an antibody used in a process of this invention is a bifunctional antibody that possesses immunospecificity for more than one target. Bifunctional antibodies and means for preparing such antibodies are well known in the art. A preferred such bifunctional antibody will have catalytic activity as set forth above as well as immunospecificity for a defined target cell. Preferably, the antibody will specifically immunoreact with a define antigen located on the surface of a target cell such as a tumor cell or a virus-infected cell. In this way, the catalytic activity is delivered specifically to a target cell and conversion of the prodrug to a drug occurs in the immediate vicinity of the desired target. A process of this invention can thus be used for targeted drug delivery.

A process of this invention can be used in vitro, in situ or in vivo to convert an inactive to an active molecule. The inactive molecule to be converted to an active molecule is exposed to the catalytic agent and maintained for a period of time and under circumstances required for cleavage of the blocking moiety off the inactive molecule and formation of the active molecule. Such conditions and times are well known to one of skill in the art. Where the catalytic agent is a catalytic antibody or bifunctional antibody, delivery of the agent to the target molecule can also be accomplished using recombinant technology and polynucleotides that encode such antibodies or fragments thereof. FIG. 9 gives the nucleotide and amino acid residue sequence of the catalytic fragment of antibody 38C2. FIG. 10 gives the nucleotide and amino acid residue sequence of the catalytic fragment of antibody 33F12. A skilled artisan can insert these polynucleotides into suitable expression vectors using standard techniques well known in the art to produce the catalytic fragments. Using such vectors, a process of the present invention can be used in gene therapy applications to transform target cells or tissues.

The Examples that follow illustrate preferred embodiments of the present invention and are not limiting of the specification and claims in any way.

EXAMPLE 1

Preparation of a Doxorubicin Prodrug Compound

All reactions requiring anhydrous conditions were performed in oven-dried glassware under an Ar or $N_2$ atmosphere. Chemicals and solvents were either puriss p.A. or purified by standard techniques. THF was distilled from sodium-benzophenone. Thin layer chromatography (TLC): silica gel plates Merck 60 $F_{254}$, compounds were visualized by irradiation with UV light and/or by treatment with a solution of 22.7 ml p-anisaldehyde, 10 ml glacial acetic acid, 33.5 ml of 98% sulfuric acid, and 906 ml of 95% EtOH followed by heating.—Flash chromatography (FC): silica gel Merck 60 (particle size 0.040–0.063 mm), eluent given in parentheses.—$^1$H NMR: Bruker AMX 400. The chemical shifts are given in δ relative to TMS (δ=0 ppm), the coupling constants J are given in Hz. The spectra were recorded in $CDCl_3$ as solvent at room temperature unless stated otherwise.—BR-MS: liquid secondary ionization (LSI-MS): VG ZAB-ZSE with 3-nitrobenzyl alcohol matrix.

Synthesis of Linkers and Prodrugs

Compound 1

2-Methylallylmagnesium chloride (0.5 M solution in THF, 22.7 ml, 11.4 mmol) was added dropwise to a stirred solution of 4-hydroxy-2-butanone (500 mg, 5.7 mmol) in THF at −78° C. The mixture was stirred for 10 min, allowed to warm to room temperature, poured over ice and extracted with ether. The product was purified by column chromatography on silica gel (ethyl acetate/hexane 50:50) to give compound 1 (680 mg, 81%). 1H NMR (400 MHz, $CDCl_3$) δ 4.94 (s, 1H), 4.74 (s, 1H), 3.90 (m, 1H), 3.86 (m, 1H), 2.84 (br, 1H), 2.49 (br, 1H), 2.30 (d, J=10.4 Hz, 1H), 2.18 (d, J=10.4 Hz, 1H), 1.83 (s, 3H), 1.81 (m, 1H), 1.69 (m, 1H).

Compound 2 p-Nitrophenyl chloroformate (605 mg, 3 mmol) was dissolved in 10 ml of methylene chloride and added dropwise to a stirred solution of compound 1 (432 mg, 3.0 mmol) in 20 ml of methylene chloride and 2 ml of triethylamine. The mixture was stirred for 60 min and the solvent was removed under reduced pressure. The product was purified by column chromatography on silica gel (ethyl acetate/hexane 75:25) to give compound 2 (583 mg, 63%). 1H NMR (400 MHz, $CDCl_3$) δ 8.27 (d, J=7.2 Hz, 2H), 7.38 (d, J=7.2 Hz, 2H), 4.98 (s, 1H), 4.79 (s, 1H), 4.49 (m, 2H), 2.38 (d, J=10.8 Hz, 1H), 2.19 (d, J=10.8 Hz, 1H), 1.97 (m, 2H), 1.86 (s, 3H), 1.27 (s, 3H).

Linker 3

Compound 2 (309 mg, 1.0 mmol) was dissolved in methylene chloride and osmium tetraoxide (2.5% solution in t-butanol, 1.25 ml, 0.1 mmol) and 4-methylmorpholine N-oxide (50% solution in water, 228 μl, 1.1 mmol) was added. The mixture was stirred for about 1 hr (TLC confirmed the disappearance of all starting material). Lead tetraacetate (490 mg, 1.1 mmol) was added, the mixture was stirred for 5 min and the solvent was separated from the solids and was removed under reduced pressure. The remaining residue was purified by column chromatography over silica gel (ethyl acetate/hexane 70:20) to give linker 3 (305 mg, 98%). 1H NMR (400 MHz, $CDCl_3$) δ 8.27 (d, J=7.2 Hz, 2H), 7.37 (d, J=7.2 Hz, 2H), 4.44 (m, 2H), 4.00 (s, 1H), 2.82 (d, J=14.0 Hz, 1H), 2.58 (d, J=14.0 Hz, 1H), 2.20 (s, 3H), 1.96 (m, 2H), 1.24 (s, 3H).

Linker 4

4-Methylamino-butyric acid hydrochloride salt (153.5 mg, 1.0 mmol) was dissolved in 1 ml of methanol and triethylamine (210 μl, 1.5 mmol). Linker 3 (311 mg, 1.0 mmol) dissolved in 1 ml of methanol was added to the reaction mixture. The mixture was stirred for 16 hr. Following removal of the solvent, the product was purified by column chromatography over silica gel (ethyl acetate/acetic acid 97:3) to give linker 4 (285 mg, 98%). 1H NMR (400 MHz, CDCl$_3$) δ 4.21 (t, J=5.2 Hz, 3H), 3.33 (m, 2H), 2.88 (br, 3H), 2.64 (t, J=14.0 Hz, 2H), 2.35 (m, 2H), 2.18 (s, 3H), 1.89 (m, 4H), 1.25 (s, 3H).

Prodrug 5

Doxorubicin hydrochloride (Fluka, Buchs, Switzerland; 10 mg, 0.017 mmol) was dissolved in 1 ml of DMF and triethylamine (3.5 μl, 0.025 mmol). Linker 3 (7.8 mg, 0.025 mmol) was dissolved in minimal amount of DMF and added to the reaction vessel. The mixture was stirred for 16 hr, after which the solvent was removed under reduced pressure. The remaining residue was dissolved in ethyl acetate, filtered, and purified by column chromatography over silica gel (ethyl acetate/methanol 90:10) to give prodrug 5 (9.5 mg, 78%). NMR indicates that prodrug 5 exists as mixture of two diastereoisomers. HRMS (MH$^+$) calcd for $C_{35}H_{41}NO_{15}$: 716.2554, obs 716.2528.

Prodrug 8

Camptothecin (Aldrich, Milwaukee, Wis.; 35 mg, 0.1 mmol) was suspended in 5 ml of acetonitrile, linker 4 (29 mg, 0.1 mmol) was added followed by DIPC (24 μl, 0.15 mmol) and DMAP (24 mg, 0.2 mmol). The mixture was stirred for 16 hr, the solvent was removed and the product purified by column chromatography over silica gel (ethyl acetate/methanol 95:5) to give prodrug 8 (42 mg, 67%). NMR indicated that prodrug 8 exists as mixture of two diastereoisomers. HRMS (MH$^+$) calcd for $C_{33}H_{37}N_3O_9$: 619.2502, obs 619.2511.

Antibody preparation. The generation and purification of mouse mAb 38C2 was described previously. A stock solution of 15 mg/ml (100 μM) 38C2 IgG in PBS (pH 7.4), stored at 4° C., was used. Antibody 38C2 is commercially available from Aldrich.

Kinetic analysis. All antibody reactions were carried out in PBS (pH 7.4) at 37° C. in microfuge tubes. Reactions were typically carried out in concentrations between 20–200 μM of substrate and 5 μM antibody concentration. Kinetic data were derived from Lineweaver-Burk plots. Antibody-catalyzed reactions were monitored at 254 nm by RP-HPLC (Hitachi L-6200A equipped with an AS-2000 autosampler and a Supelcosil LC-18 column (25 cm×4.6 mm, 5 m) using various proportions of acetonitrile:water at 1 ml/min.

Cell lines. Human colon carcinoma cell lines HT29 and LIM1215 were kindly provided by Dr. Lloyd J. Old from The Ludwig Institute for Cancer Research in New York. Human prostate cancer cell line LNCap was purchased from American Type Culture Collection (Manassas, Va.). All cell lines were maintained in RPMI 1640 medium (Hyclone, Logan, Utah) supplemented with 10% fetal bovine serum (Life Technologies, Gaithersburg, Md.) and antibiotic-antimycotic reagents (Life Technologies) containing penicillin, streptomycin, and amphotericin B. The cell lines were cultivated in culture flasks at 37° C. in a humidifying incubator in an atmosphere of 5% $CO_2$.

Cell growth inhibition assays Stock solutions of 5 mM doxorubicin and prodoxorubicin in DMF, respectively, were stored at 4° C. For cell growth inhibition assays, 250-μM dilutions of doxorubicin and prodoxorubicin in PBS (pH 7.4) were freshly prepared from the 5 mM stock solutions and further diluted in cell culture medium to yield 10 nM to 25 μM solutions. Methyl vinyl ketone was purchased from Aldrich (Milwaukee, Wis.). Stock solutions of 1 mM camptothecin and procamptothecin in DMF, respectively, were stored at 4° C. For cell growth inhibition assays, 100-μM dilutions of camptothecin and procamptothecin in PBS (pH 7.4) were freshly prepared from the 1 mM stock solutions and further diluted in cell culture medium to yield 10 nM to 1 μM solutions. Cells grown in culture flasks were trypsinized, washed with PBS, resuspended in cell culture medium, and reduced to a single cell suspension by passing through a 18 G needle. After counting, the cells were plated at a density of 5×10$^3$ (HT29) or 1×10$^4$ (LIM1215, LNCap) cells/well in 96-well tissue culture plates and maintained in culture as described above. Drugs were diluted to a final concentration range of 10 nM to 25 μM in 100 μl 10% fetal bovine serum in RPMI 1640 and added to the cells 24 hours after plating. In case of the antibody experiments, prodrug and 38C2 IgG were mixed just before adding to the cells. After drug addition, the cells were maintained at 37° C. in 5% $CO_2$ for 3 to 5 days (72 to 120 hours). Prior to the quantitative cell growth inhibition assay, the cell density was qualitatively analyzed by microscopy. This visual evaluation always matched the result of the quantitative analysis. The cells were then washed with 150 μl PBS (pH 7.5) and incubated with 100 μl of 9% (v/v) Triton-X 100 (Sigma, St. Louis, Mo.) for 45 minutes at 37° C. The supernatant was then transferred to a 96-well V-shaped plate and centrifuged to remove cell debris. In a 96-well plate, 50 μl of the supernatants were combined with 50 μl of freshly reconstituted substrate reaction mixtures containing 2-(p-iodophenyl)-3-(p-nitrophenyl)-5-phenyltetrazolium chloride that is converted into a red formazan product in the presence of lactate dehydrogenase released from the cells. The substrate reaction mixture was purchased from Promega (Madison, Wis.). The color reaction was incubated for 5 to 15 minutes at room temperature and then stopped by adding 50 μl of 1 M acetic acid. For quantification, 50 μl aliquots were transferred to another 96-well plate and the color was read at 490 nm in an ELISA plate reader. The absorbance data were converted to percent cell density with the untreated controls being 100% and the background of the color reaction being 0%.

In vivo activity assay. Mice were injected intravenously (tail vein) with 100 μl of 15 mg/ml 38C2 IgG in PBS or the same amount of a control antibody. Blood samples were obtained every 24 h and sera were prepared by centrifugation. To a final volume of 100 μl, 5 μl serum (final concentration 1:20) were mixed with 93 μl PBS and 2 μl 5 mM methodol (final concentration 100 μM). Product formation was followed with a fluorescence plate-reader by monitoring at $\lambda_{abs}$=330 nm and $\lambda_{em}$=452 nm (List et al., 1998b). Using SOFTmax Pro software (Molecular Devices; Sunnyvale, Calif.), specific activities were determined from the time range 2000 to 5000 s after reaction start. For a standard, specific activities were also derived from defined concentrations of 38C2 IgG. Concentrations in the range of 50 nM to 500 nM were in linear proportion with the initial rates and were used to derive the serum concentration of 38C2 IgG from specific activities by linear regression analysis.

Design and synthesis of a generic drug masking trigger. The products of aldol reactions are ketones and aldehydes. Thus, in isolation, aldol chemistry is of little utility for drug masking/activation strategies. The present invention is based on a tandem retro-aldol-retro-Michael reaction catalyzed by antibody 38C2. The finding that antibody 38C2 catalyzes the retro-Michael reaction of β-heterosubstituted ketones and aldehydes to generate free amine, hydroxy, and thiol groups supports the concept of a prodrug activation catalyzed by antibody 38C2. Many drugs contain free amine, hydroxy, or thiol groups whose masking often results in a significant decrease of the activity. Due to the high background rate of the retro-Michael reaction, however, retro-Michael substrates themselves are generally not suitable as prodrugs.

This problem could be solved with a tandem reaction. In this reaction scheme, the carbon-carbon bond-cleaving retro-aldol reaction is used to reveal a hidden retro-Michael substrate. This allows the coupling of the low background reaction inherent in the aldol with the versatile carbon-heteroatom bond cleavage chemistry of the retro-Michael reaction.

Figure 2:
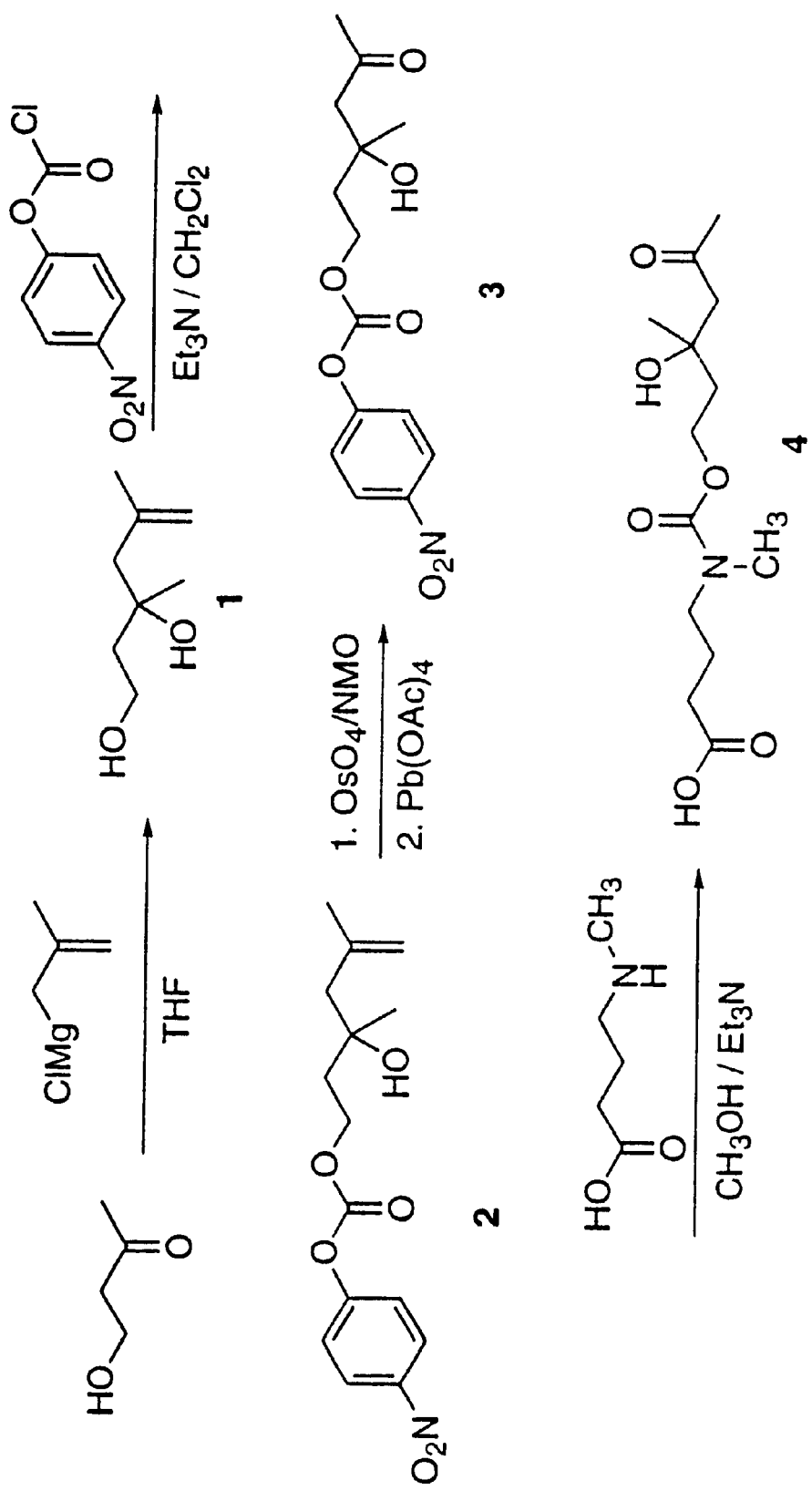
FIG. 2 shows synthesis of generic linkers 3 and 4 which can be used to mask functionally active amine and hydroxy groups of drugs, respectively.

By linking the retro-Michael reaction to an upstream retro-aldol reaction in a fluorogenic substrate, where both reactions are catalyzed by antibody 38C2, significant enhancements in the $k_{cat}/k_{uncat}$ ratio (List, B., Barbas, C. F., III & Lerner, R. A. (1998) *Proc. Natl. Acad. Sci.* USA 95, 15351–15355) have been demonstrated. Based on these results generic heteroatom-masking linkers were designed that are recognized and cleaved by antibody 38C2, leading to free drug release (FIG. 1). The synthesis of linkers 3 and 4 for the masking of amine and hydroxy groups, respectively, is shown in FIG. 2. Three examples of antibody-mediated prodrug activation have been reported in the literature (Miyashita, H., Karaki, Y., Kikuchi, M. & Fujii, I. (1993) *Proc. Natl. Acad. Sci.* USA 90, 5337–5340, Campbell, D. A., Gong, B., Kochersperger, L. M., Yonkovich, S., Gallop, M. A. & Schultz, P. G. (1994) *J. Am. Chem. Soc.* 116, 2165–2166, Wentworth, P., Datta, A., Blakey, D., Boyle, T., Partridge, L. J. & Blackburn, G. M. (1996) *Proc. Natl. Acad. Sci.* USA 93, 799–803 3–5). All of these reports use tetrahedral phosphonates as stable transition state analogs for antibody generation. Prodrug activation, i.e. release of the free drug, was achieved by hydrolysis of an ester or a carbamate. Many endogenous enzymes catalyze these types of reactions. Further, immunization with transition state analogs generates antibodies that are generally highly specific for their designed substrates. Therefore, this approach is usually applicable to the activation of a single prodrug. By contrast, this approach is based on an antibody prepared using reactive immunization designed to allow for the generic masking/activation of potentially any drug that contains a functionally active heteroatom.

Design and synthesis of a doxorubicin prodrug that is a substrate for antibody 38C2. Topoisomerase I and II inhibitor doxorubicin was chosen as a model compound for this prodrug activation concept because its structure activity relationship is well characterized and it has been used previously in ADEPT systems (Niculescu-Duvaz, I. & Springer, C. J. (1997) *Adv. Drug Delivery Rev.* 26, 151–172). Doxorubicin is a drug approved for cancer therapy that suffers from misdirected toxicity. As a candidate prodrug of doxorubicin, subsequently referred to as prodoxorubicin, the carbamate derivative 5 was synthesized in one step from commercially available doxorubicin 7 and linker 3. Antibody 38C2 was found to catalyze both reactions of the retro-aldol-retro-Michael cascade cleavage of prodoxorubicin 5 leading to the release of free doxorubicin 7 and acetone, methyl vinyl ketone, and carbon dioxide as by-products (FIG. 3). The tertiary aldol was chosen as the first reaction since no known natural enzyme catalyzes this particular type of retro-aldol reaction. In accord with its mechanism, catalysis was completely inhibited by 2,4-pentanedione and followed Michaelis-Menten kinetics with $k_{cat}=0.00174$ min$^{-1}$, $k_{cat}/k_{uncat}>10^5$, and $K_m=43$ $\mu$M. Typically 38C2 is highly enantioselective, however, under the conditions studied, the reaction proceeded to completion indicative of loss of enantioselectivity and complete activation of the prodrug. According to a pharmacokinetic analysis of ADEPT systems, low $k_{cat}$ values combined with high $K_m$ values are expected to increase the tumor to blood ratio of the free drug, leading to a reduction in peripheral toxicity (Yuan, J., Baxter, L. T. & Jain, R. K. (1991). *Cancer Res.* 51, 3119–3130). However, despite the high $k_{cat}$ to $k_{uncat}$ ratio, it seems desirable to improve the relatively low $k_{cat}$ value for the prodoxorubicin activation. To this end, both the masking linker and catalytic antibody are being optimized.

Figure 4:
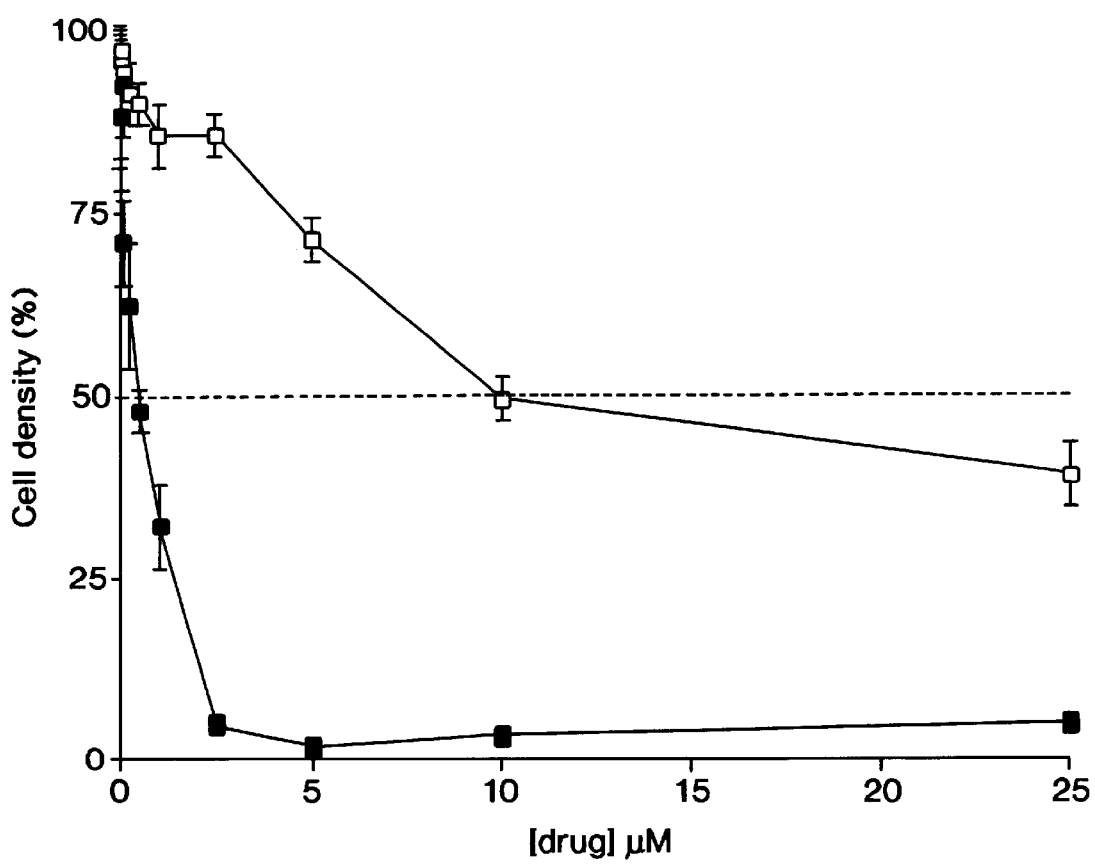
FIG. 4 shows growth inhibition of LIM1215 human colon carcinoma cells in vitro by doxorubicin (■) and prodoxorubicin (□)(Bars indicate SD; n=4). The data were determined using the assay described in FIG. 5 and are summarized in Table 1. The dashed line indicates 50% decrease in the cell density as compared to the untreated control. Note the reduced capacity of prodoxorubicin for cell growth inhibition.

Cell growth inhibition by doxorubicin and prodoxorubicin. The antiproliferative effects of drug and prodrug were monitored by quantifying the cell growth in the presence of a range of concentrations of doxorubicin and prodoxorubicin, respectively. Three different human cancer cell lines were evaluated, human colon carcinoma cell lines HT29 and LIM1215 and human prostate cancer cell line LNCap. The cells were lysed 72 h or 120 h after drug addition and the activity of the cytoplasmic enzyme lactate dehydrogenase released from the cells was assayed using a color reaction. The lactate dehydrogenase activity correlated with the cell growth as revealed by microscopic analysis and gave consistent readings as revealed by standard deviations smaller than 10% in quadruplicate assays. The inhibition of cell growth of LIM1215 cells 120 h after addition of doxorubicin and prodoxorubicin is shown (FIG. 4). The results of studies of three cancer cell lines at the two different time points are summarized in Table 1, below.

TABLE 1

| | | $IC_{50}$ in $\mu M$[1] | | |
|---|---|---|---|---|
| Time | Treatment | HT 29 | LIM1215 | LNCaP |
| 72h | doxorubicin | 3.0 | 0.4 | 0.4 |
| | prodoxorubicin | >25 | 18 | 18 |
| 120h | doxorubicin | 2.5 | 0.4 | 0.2 |
| | prodoxorubicin | 22 | 10 | 8 |

[1]Drug concentration that causes a 50% decrease in the cell density as compared to the untreated control.

As expected, prodoxorubicin was significantly less effective at inhibiting cell growth. The ratio between antiproliferative effects of prodoxorubicin and doxorubicin varied from about 10 in the case of HT29 cells to 40 for LNCap cells (Table 1). These ratios are in agreement with comparable anthracycline prodrugs with carbamate linkage (Niculescu-Duvaz, I. & Springer, C. J. (1997) *Adv. Drug Delivery Rev.* 26, 151–172).

Figure 5:
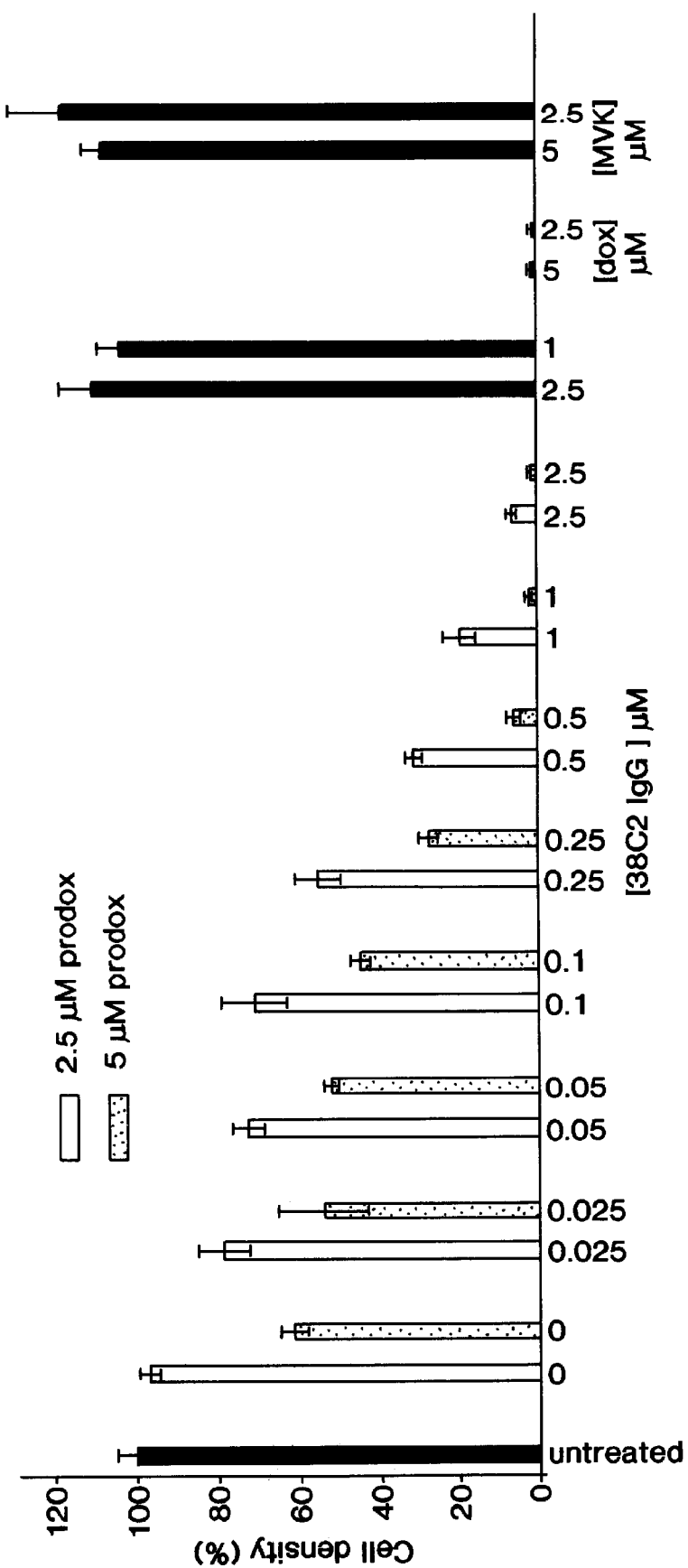
FIG. 5 shows growth inhibition of LIM1215 human colon carcinoma cells by prodoxorubicin in the presence of antibody 38C2. Cells in quadruplicate wells in a 96-well plate were lysed 120 h after drug addition and the activity of the cytoplasmic enzyme lactate dehydrogenase released from the cells was detected using a colorimetric assay. The intensity of the red color correlates with the number of cells in the well. Controls are shown in black columns. (dox= doxorubicin; prodox=prodoxorubicin; MVK=methyl vinyl ketone; bars indicate SD; n=4).

Functional activation of prodoxorubicin by antibody 38C2. The inhibition of cell growth by a combination of prodoxorubicin and antibody 38C2 was analyzed using the assay described above (FIG. 5). This analysis revealed that the combination of prodoxorubicin and antibody 38C2 strongly inhibits cell growth, whereas the same concentration of prodoxorubicin alone is far less potent. Antibody 38C2 alone does not inhibit cell growth. The results of studies of LIM1215 cells 120 h after drug addition are shown (FIG. 5). Microscopic analysis revealed that no cells survived the combined treatment. The fact that cell growth inhibition is complete for both molar ratios of substrate to antibody of 1:1 and 10:1 indicates the catalytic activation of prodoxorubicin by antibody 38C2 (FIG. 5). At even higher ratios, i.e. lower antibody concentrations, it was found that cell growth inhibition clearly correlates with the antibody concentration. A by-product of the conversion of prodoxorubicin to doxorubicin is methyl vinyl ketone, which is potentially toxic. However, no inhibition of cell growth by methyl vinyl ketone was detected when applied alone at similar concentrations. These data demonstrate that antibody 38C2 functionally activates prodoxorubicin, resulting in inhibition of cell growth. It is important to stress that despite the relatively low $k_{cat}$ value for prodoxorubicin activation, submicromolar concentrations of antibody 38C2 were found to be sufficient for effective cell growth inhibition (FIG. 5). This result compares favorably to earlier reports of prodrug activation by catalytic antibodies (Miyashita, H., Karaki, Y., Kikuchi, M. & Fujii, I. (1993) *Proc. Natl. Acad Sci. USA* 90, 5337–5340, Campbell, D. A., Gong, B., Kochersperger, L. M., Yonkovich, S., Gallop, M. A. & Schultz, P. G. (1994) *J. Am. Chem. Soc.* 116, 2165–2166, Wentworth, P., Datta, A., Blakey, D., Boyle, T., Partridge, L. J. & Blackburn, G. M. (1996) *Proc. Natl. Acad. Sci.* USA 93, 799–803).

Figure 6:
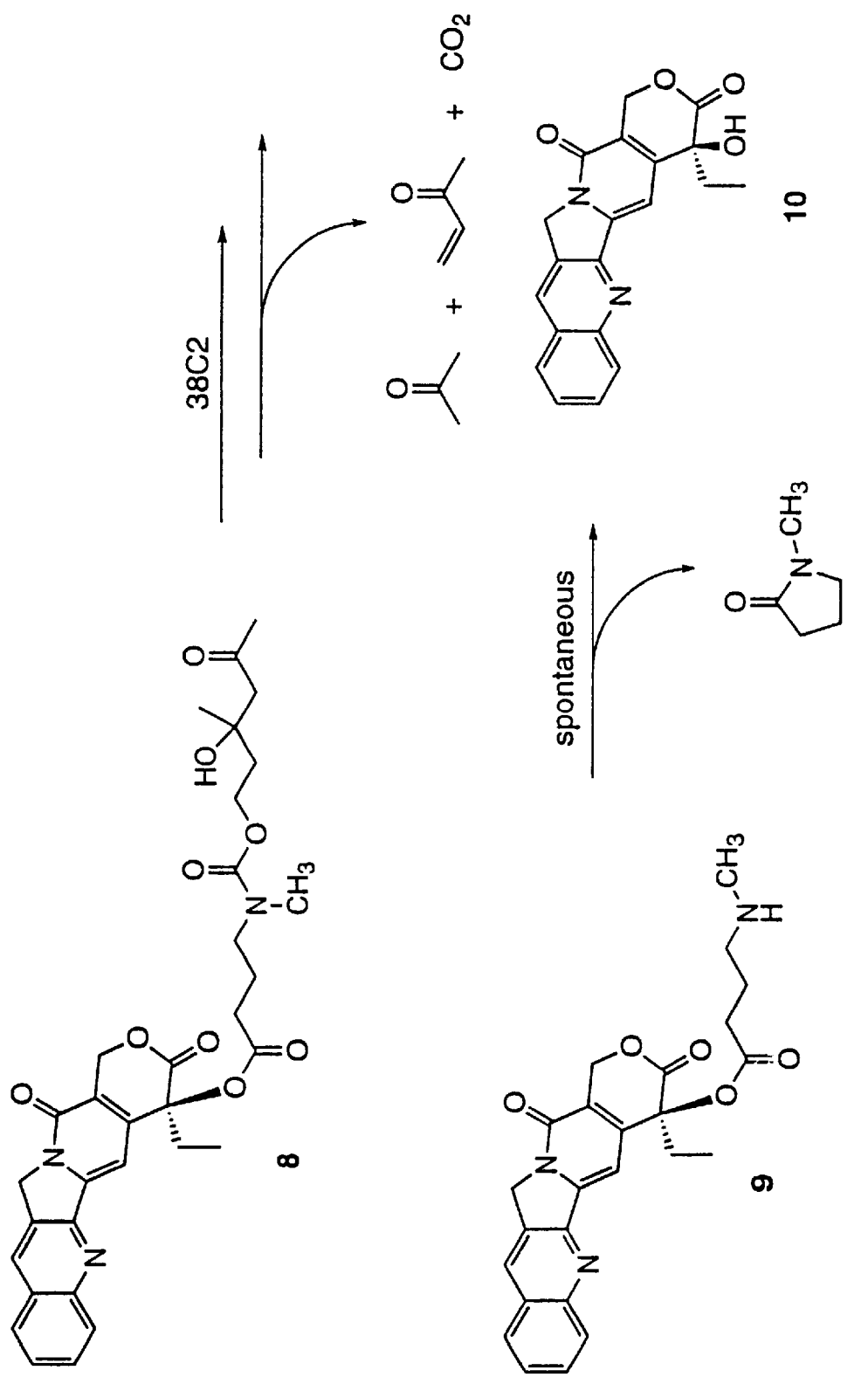
FIG. 6 shows camptothecin prodrug activation via a tandem retro-aldol-retro-Michael reaction catalyzed by antibody 38C2 followed by a spontaneous lactamization.

Design and synthesis of a camptothecin prodrug that is a substrate for antibody 38C2. In order to demonstrate the general applicability of this prodrug activation concept by masking a different drug and a different heteroatom, the powerful topoisomerase I inhibitor camptothecin was selected for modification (Potmesil, M. (1994) *Cancer Res.* 54, 1431–1439.). In contrast to doxorubicin, camptothecin has not been used in ADEPT studies before. From analysis of the structure activity relationship of camptothecin it was found that two functional groups of camptothecin (10, FIG. 6) are required for its activity; the six-membered lactone ring E and the 20-hydroxy group in a position to the lactone (Potmesil, M. (1994) *Cancer Res.* 54, 1431–1439, Greenwald, R. B., Pendri, A., Conover, C., Gilbert, C., Yang, R. & Xia, J. (1996) *J. Med. Chem.* 39, 1938–1940). It was also found that the lactone ring of camptothecin is not stable in vivo but is rapidly hydrolyzed. Maintenance of the lactone ring is essential to the activity of the drug. Esterification of the tertiary alcohol at position 20 was shown to increase the stability of the lactone ring. A few examples of camptothecin prodrugs that utilize the 20-hydroxy group in order to generate transport forms of the drug with a stabilized lactone ring, reduced toxicity, and higher solubility in water have been reported (Greenwald, R. B., Pendri, A., Conover, C., Gilbert, C., Yang, R. & Xia, J. (1996) *J. Med. Chem.* 39, 1938–1940, Wall, M. E., Wani, M. C., Nicholas, A. W., Manikumar, G., Tele, C., Moore, L., Truesdale, A., Leitner, P. & Besterman, J. M. (1993) *J. Med Chem.* 36, 2689–2700). The 20-hydroxy group was selected for masking camptothecin with this retro-aldol-retro-Michael linker. As a candidate prodrug of camptothecin, subsequently referred to as procamptothecin, the ester derivative of camptothecin 8 was synthesized in one step from commercially available camptothecin 10 and linker 4. Antibody 38C2 was found to catalyze the retro-aldol and retro-Michael reactions to give self-immolative amine 9 (FIG. 6). After spontaneous lactamization the free drug was released. As expected, the addition of the polar linker to campothecin increased its solubility in water. In the absence of antibody 38C2, the ester linkage between camptothecin and the linker was found to be much more stable than reported for other 20-hydroxy ester derivatives of camptothecin.

Figure 7:
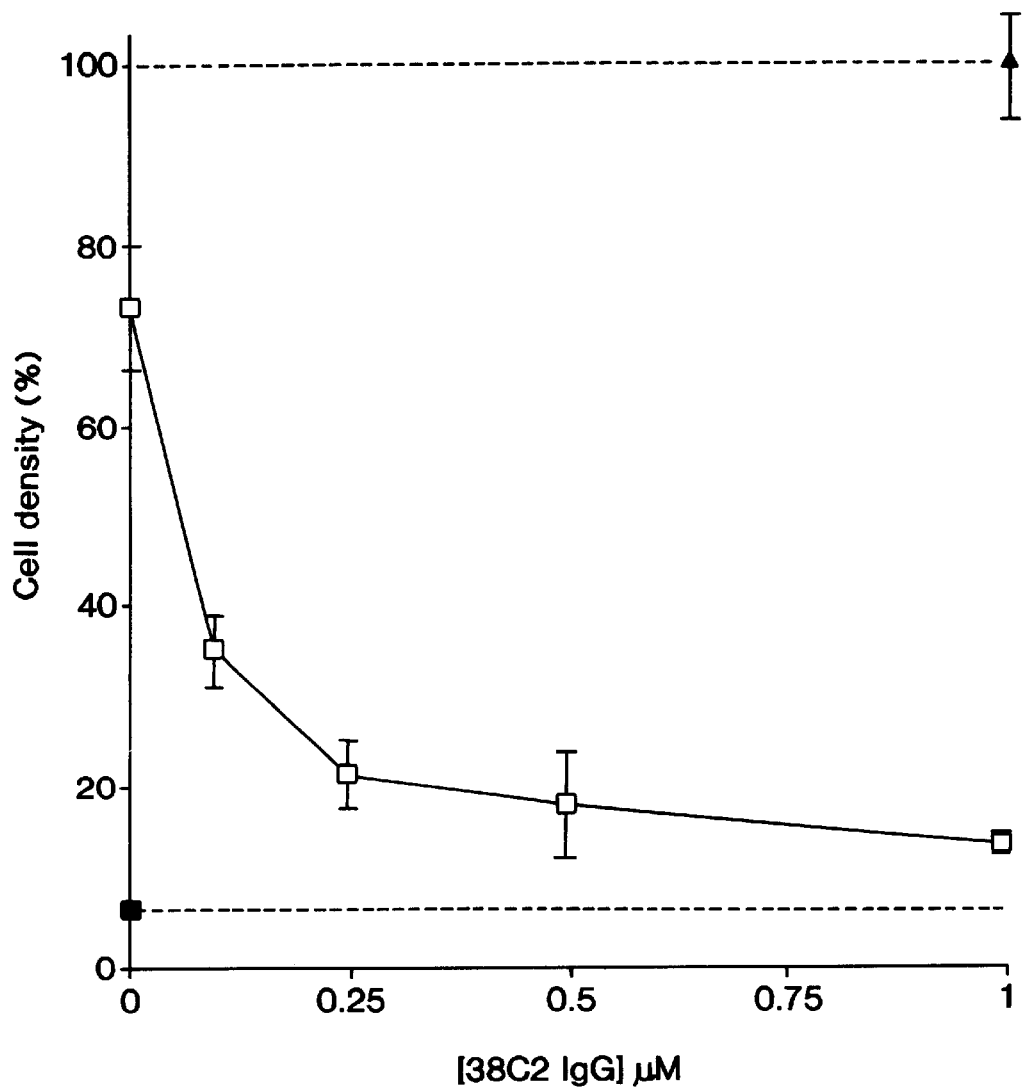
FIG. 7 shows growth inhibition of HT29 human colon carcinoma cells by procamptothecin in the presence of increasing concentrations of antibody 38C2. (▲) untreated control; (□) 1 μM procamptothecin; (■) 1 μM camptothecin; (bars indicate SD; n=4).

Biological evaluation of procamptothecin. The antiproliferative effects of camptothecin and procamptothecin were monitored by quantifying the growth of HT29, LIM1215, and LNCap cells in the presence of a range of concentrations of drug and prodrug. All camptothecin assays were analyzed 72 h after drug addition. The $IC_{50}$ values of camptothecin were in the range of 0.1 to 0.25 $\mu$M for HT29 and LIM1215 cells and 0.01 to 0.025 $\mu$M for LNCap cells, revealing that camptothecin inhibits cell growth at substantially lower concentrations than doxorubicin (Table 1). Singificantly, procamptothecin demonstrated a toxicity that was reduced by more than a factor of ten as compared to camptothecin suggesting that the ester linkage of the retro-aldol-retro-Michael mask to camptothecin is relatively stable even in cell culture medium containing serum (data not shown). This result prompted the examination of the functional activation of procamptothecin by antibody 38C2. The growth inhibition assay with HT29 cells is shown (FIG. 7). Antibody 38C2 activated procamptothecin in a concentration-dependent manner revealing the full toxic effect of the drug. This activation was also seen in assays with LIM1215 and LNCap cells. Intriguingly, a concentration as low as 0.1 $\mu$M 38C2 IgG was highly effective in inhibiting cell growth (FIG. 7). This result is relevant to the potential in vivo applications of our prodrug activation system. The local concentration of antibody 38C2 that can be achieved at the tumor site through a tumor-targeting moiety conjugated to antibody 38C2 is likely to be in the submicromolar range depending on the accessibility of the target antigen, its expression level, and its affinity for the tumor-targeting moiety. An optimized combination of prodrugs that can be activated by antibody 38C2 may increase the sensitivity further.

Figure 8:
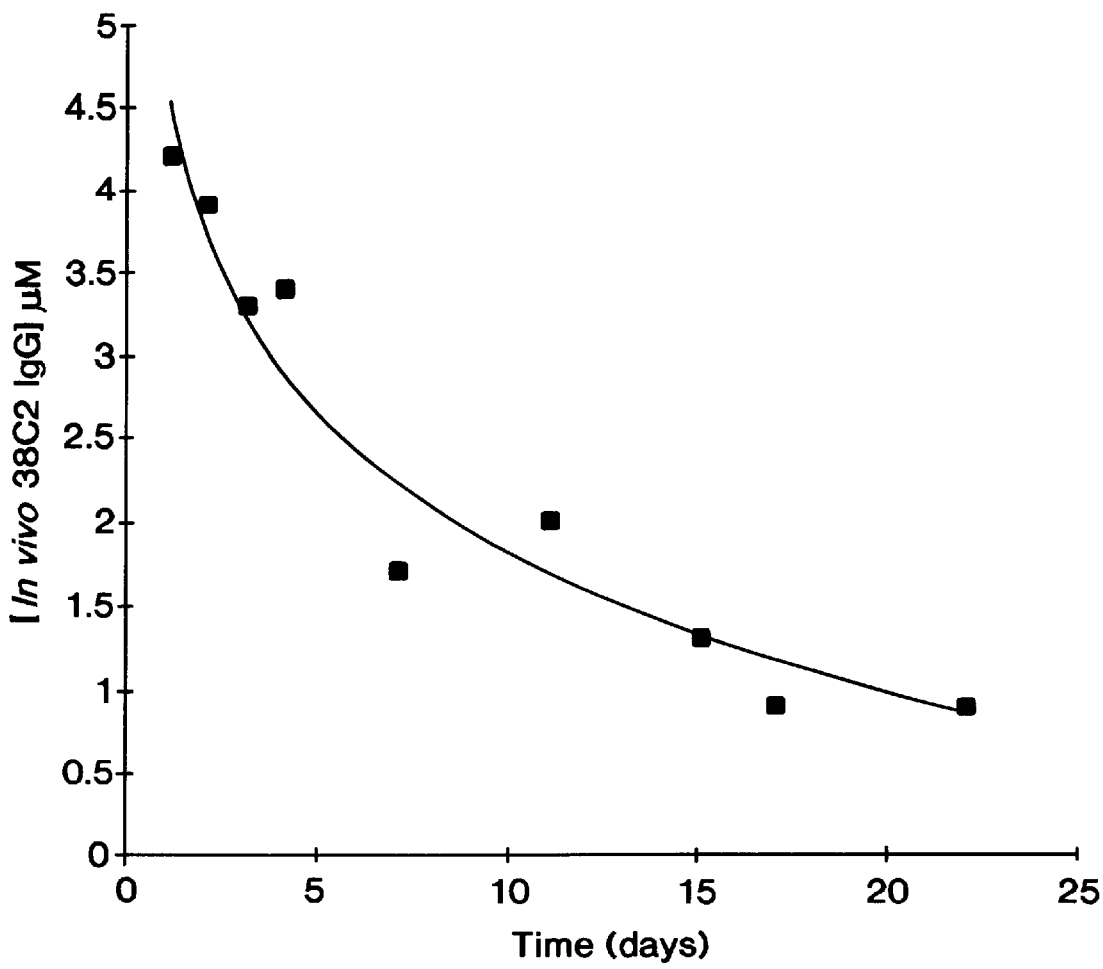
FIG. 8 shows in vivo activity of antibody 38C2. Mice were injected with 100 μl of 15 mg/ml 38C2 IgG in PBS on day 0. The concentration of 38C2 IgG in mouse sera was studied as a function of time after the injection. Activity was calculated based on the antibody 38C2-catalyzed conversion of the fluorogenic aldol sensor methodol into fluorescent 6-methoxy-2-naphtaldehyde (11). Typical data derived from one mouse are shown. The initial 38C2 IgG concentration on day 0 can be estimated to be about 6 μM based on a blood volume of 1.5 ml and 1.5 mg injected antibody. Catalysis was not detectable in sera from mice injected with 100 μl of 15 mg/ml control antibody in PBS.

In vivo activity of antibody 38C2. As an evaluation of the in vivo relevance of this prodrug activation concept, 38C2 IgG was injected intravenously into mice and sera was prepared after defined time points and analyzed for catalytic activity. Using the highly sensitive conversion of the fluorogenic aldol sensor methodol into fluorescent 6-methoxy-2-napthaldehyde (List, B., Barbas, C. F., III & Lerner, R. A. (1998) *Proc. Natl. Acad. Sci.* USA 95, 15351–15355), catalytic activity was detectable only in mice that had been treated with antibody 38C2. No catalytic activity was detectable in sera from mice treated with the same amount of a control antibody. This result again confirms the stability of retro-aldol substrates of antibody 38C2 in the absence of the antibody, a prerequisite for our prodrug activation concept. Using defined concentrations of 38C2 IgG as a standard, the in vivo concentration of 38C2 IgG was calculated from its catalytic activity. As shown in FIG. 8, 38C2 IgG was detectable for more than three weeks with a clearance rate typical of an IgG in vivo. This result demonstrates that antibody 38C2 retains its catalytic activity over therapeutically relevant time periods in vivo. Potential in vivo problems like rapid clearance or inhibition of the catalytic activity of 38C2 by covalently binding diketones or other potential inhibitors were not observed. Moreover, mice treated with antibody 38C2 did not show any apparent abnormalities suggesting that the antibody is not toxic.

A system was developed that includes a drug masking strategy and a complementary catalytic antibody for prodrug activation that demonstrates characteristics of the ideal ADEPT system. These characteristics include a novel and versatile masking chemistry that may be applied to a wide range of drugs. Application of this masking strategy to two drugs suitable for human cancer therapy produced novel prodrugs with favorable toxicity ratios. No known enzyme possesses the catalytic activity required for the activation of these prodrugs, however, activation of diverse prodrugs structures may be achieved with the broad scope catalytic antibody 38C2. These unique features will allow treatment regimes involving cocktails of prodrugs to be studied. Antibody 38C2 demonstrated long-lived catalytic activity in vivo and was shown to selectively activate prodrugs and potentiate killing of colon and prostate cancer cell lines when applied at therapeutically relevant concentrations in culture. Humanization of 38C2 should endow the final characteristic of immunosilence to the antibody allowing the exploration of the potential of this system for the selective targeting of tumors and their supporting vasculature. A gene encoding a humanized 38C2 should also find application in gene therapy strategies allowing for the selective ablation of cells expressing it.

SEQUENCE LISTING

<160> NUMBER OF SEQ ID NOS: 6

<210> SEQ ID NO: 1
<211> LENGTH: 899
<212> TYPE: DNA
<213> ORGANISM: Mus musculus
<220> FEATURE:
<221> NAME/KEY: CDS
<222> LOCATION: (1)..(897)

<400> SEQUENCE: 1

```
ggt ttc gct acc gtt gct cag gct gct cac cat cac cac cat gtg      48
Gly Phe Ala Thr Val Ala Gln Ala Ala His His His His His Val
 1               5                  10                  15 gcc cag gcg gcc agt tcc gag ctc gac att gtg atg acc cag tct cca  96
Ala Gln Ala Ala Ser Ser Glu Leu Asp Ile Val Met Thr Gln Ser Pro
             20                  25                  30 ctc tcc ctg cct gtc cgt ctt gga gat caa gcc tcc atc tct tgc aga  144
Leu Ser Leu Pro Val Arg Leu Gly Asp Gln Ala Ser Ile Ser Cys Arg
         35                  40                  45 tct agt cag agc ctt cta cac act tat gga agc ccc tat tta aat tgg  192
Ser Ser Gln Ser Leu Leu His Thr Tyr Gly Ser Pro Tyr Leu Asn Trp
     50                  55                  60 tac ctg cag aag cca ggc cag tcg cca aag ctc ctg atc tac aaa gtt  240
Tyr Leu Gln Lys Pro Gly Gln Ser Pro Lys Leu Leu Ile Tyr Lys Val
 65                  70                  75                  80 tcc aac cgc ttt tct ggg gtc cca gac agg ttc agt ggc agt gga tca  288
Ser Asn Arg Phe Ser Gly Val Pro Asp Arg Phe Ser Gly Ser Gly Ser
                 85                  90                  95 ggg aca gat ttc aca ctc agg atc agc aaa gtg gag gct gag gat ctg  336
Gly Thr Asp Phe Thr Leu Arg Ile Ser Lys Val Glu Ala Glu Asp Leu
            100                 105                 110 gga gtt tat ttc tgc tct caa ggt aca cat ctt ccg tac acg ttc gga  384
Gly Val Tyr Phe Cys Ser Gln Gly Thr His Leu Pro Tyr Thr Phe Gly
        115                 120                 125 ggg ggg acc aag ctg gaa ata aaa tcc tct ggt ggc ggt ggc tcg ggc  432
Gly Gly Thr Lys Leu Glu Ile Lys Ser Ser Gly Gly Gly Gly Ser Gly
    130                 135                 140 ggt ggt ggg ggt ggt tcc tct aga tct tcc ctc gag gtg atg ttg gtg  480
Gly Gly Gly Gly Gly Ser Ser Arg Ser Ser Leu Glu Val Met Leu Val
145                 150                 155                 160 gag tct gga gga ggc ttg gtg caa cct gga gga acc atg aaa ctc tcc  528
Glu Ser Gly Gly Gly Leu Val Gln Pro Gly Gly Thr Met Lys Leu Ser
                165                 170                 175 tgt gaa att tct gga tta act ttc aga aat tat tgg atg tct tgg gtc  576
Cys Glu Ile Ser Gly Leu Thr Phe Arg Asn Tyr Trp Met Ser Trp Val
            180                 185                 190 cgc cag tct cca gag aag ggg ctt gag tgg gtt gct gaa att aga ttg  624
Arg Gln Ser Pro Glu Lys Gly Leu Glu Trp Val Ala Glu Ile Arg Leu
        195                 200                 205 aga tct gat aat tat gca aca cat tat gcg gag tct gtg aaa ggg aag  672
Arg Ser Asp Asn Tyr Ala Thr His Tyr Ala Glu Ser Val Lys Gly Lys
    210                 215                 220 ttc acc atc tca aga gat gat tcc aaa agt cgt ctc tac ctg caa atg  720
Phe Thr Ile Ser Arg Asp Asp Ser Lys Ser Arg Leu Tyr Leu Gln Met
225                 230                 235                 240 aac agc tta aga act gaa gac act gga att tat tac tgt aaa acc tat  768
Asn Ser Leu Arg Thr Glu Asp Thr Gly Ile Tyr Tyr Cys Lys Thr Tyr
                245                 250                 255
```

```
ttt tac tca ttt tct tac tgg ggc caa ggg act ctg gtc act gtc tct    816
Phe Tyr Ser Phe Ser Tyr Trp Gly Gln Gly Thr Leu Val Thr Val Ser
            260                 265                 270 gca gcc tcc aca cag agc cca tcc gtc act agt ggc cag gcc ggc cag    864
Ala Ala Ser Thr Gln Ser Pro Ser Val Thr Ser Gly Gln Ala Gly Gln
        275                 280                 285 tac ccg tac gac gtt ccg gac tac gct tct taa aa                     899
Tyr Pro Tyr Asp Val Pro Asp Tyr Ala Ser
    290                 295
```

<210> SEQ ID NO: 2
<211> LENGTH: 298
<212> TYPE: PRT
<213> ORGANISM: Mus musculus

<400> SEQUENCE: 2

```
Gly Phe Ala Thr Val Ala Gln Ala Ala His His His His His Val
 1               5                  10                  15

Ala Gln Ala Ala Ser Ser Glu Leu Asp Ile Val Met Thr Gln Ser Pro
            20                  25                  30

Leu Ser Leu Pro Val Arg Leu Gly Asp Gln Ala Ser Ile Ser Cys Arg
        35                  40                  45

Ser Ser Gln Ser Leu Leu His Thr Tyr Gly Ser Pro Tyr Leu Asn Trp
    50                  55                  60

Tyr Leu Gln Lys Pro Gly Gln Ser Pro Lys Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Arg Ile Ser Lys Val Glu Ala Glu Asp Leu
            100                 105                 110

Gly Val Tyr Phe Cys Ser Gln Gly Thr His Leu Pro Tyr Thr Phe Gly
        115                 120                 125

Gly Gly Thr Lys Leu Glu Ile Lys Ser Ser Gly Gly Gly Ser Gly
    130                 135                 140

Gly Gly Gly Gly Ser Ser Arg Ser Ser Leu Glu Val Met Leu Val
145                 150                 155                 160

Glu Ser Gly Gly Gly Leu Val Gln Pro Gly Gly Thr Met Lys Leu Ser
                165                 170                 175

Cys Glu Ile Ser Gly Leu Thr Phe Arg Asn Tyr Trp Met Ser Trp Val
            180                 185                 190

Arg Gln Ser Pro Glu Lys Gly Leu Glu Trp Val Ala Glu Ile Arg Leu
        195                 200                 205

Arg Ser Asp Asn Tyr Ala Thr His Tyr Ala Glu Ser Val Lys Gly Lys
    210                 215                 220

Phe Thr Ile Ser Arg Asp Asp Ser Lys Ser Arg Leu Tyr Leu Gln Met
225                 230                 235                 240

Asn Ser Leu Arg Thr Glu Asp Thr Gly Ile Tyr Tyr Cys Lys Thr Tyr
                245                 250                 255

Phe Tyr Ser Phe Ser Tyr Trp Gly Gln Gly Thr Leu Val Thr Val Ser
            260                 265                 270

Ala Ala Ser Thr Gln Ser Pro Ser Val Thr Ser Gly Gln Ala Gly Gln
        275                 280                 285

Tyr Pro Tyr Asp Val Pro Asp Tyr Ala Ser
    290                 295
```

<210> SEQ ID NO: 3

```
<211> LENGTH: 856
<212> TYPE: DNA
<213> ORGANISM: Artificial Sequence
<220> FEATURE:
<223> OTHER INFORMATION: Description of Artificial Sequence: Nucleotide
      residue sequence of catalytic fragment.
<221> NAME/KEY: CDS
<222> LOCATION: (1)..(855)

<400> SEQUENCE: 3 gct acc gtt gct cag gct gct cac cat cac cat cac cat gtg gcc cag        48
Ala Thr Val Ala Gln Ala Ala His His His His His His Val Ala Gln
 1               5                  10                  15 gcg gcc agt tcc gag ctc gat gtt gtg atg acc cag act cca ctc tcc        96
Ala Ala Ser Ser Glu Leu Asp Val Val Met Thr Gln Thr Pro Leu Ser
             20                  25                  30 ctg cct gtc agt ctt gga gat caa gcc tcc atc tct tgc aga tct agt       144
Leu Pro Val Ser Leu Gly Asp Gln Ala Ser Ile Ser Cys Arg Ser Ser
         35                  40                  45 cag agc ctt gta cac agt tat gga aac acc ttt tta aat tgg tac ctg       192
Gln Ser Leu Val His Ser Tyr Gly Asn Thr Phe Leu Asn Trp Tyr Leu
     50                  55                  60 cag aag tca ggc cag tct cca aag ctc ctg atc tac aaa gtt tcc aac       240
Gln Lys Ser Gly Gln Ser Pro Lys Leu Leu Ile Tyr Lys Val Ser Asn
 65                  70                  75                  80 cga ttt tct ggg gtc cca gac agg ttc agt ggc agt gga tca ggg aca       288
Arg Phe Ser Gly Val Pro Asp Arg Phe Ser Gly Ser Gly Ser Gly Thr
                 85                  90                  95 gat ttc aca ctc aag atc agc aga gtg gag gct gag gat ctg gga gtt       336
Asp Phe Thr Leu Lys Ile Ser Arg Val Glu Ala Glu Asp Leu Gly Val
            100                 105                 110 tat ttc tgc tct caa ggt aca cat gtt ccg tac acg ttc gga ggg ggg       384
Tyr Phe Cys Ser Gln Gly Thr His Val Pro Tyr Thr Phe Gly Gly Gly
        115                 120                 125 acc aag ctg gag ctg aaa tcc tct ggt ggc ggt ggc tcg ggc ggt ggt       432
Thr Lys Leu Glu Leu Lys Ser Ser Gly Gly Gly Gly Ser Gly Gly Gly
    130                 135                 140 ggg ggt ggt tcc tct aga tct tcc ctc gag gtg atg ctg gtg gag tct       480
Gly Gly Gly Ser Ser Arg Ser Ser Leu Glu Val Met Leu Val Glu Ser
145                 150                 155                 160 gga gga ggc ttg gtg caa cct gga gga tcc atg aaa ctc tcc tgt gtg       528
Gly Gly Gly Leu Val Gln Pro Gly Gly Ser Met Lys Leu Ser Cys Val
                165                 170                 175 gtg tct gga tta acc ttc agt aga ttc tgg atg tct tgg gtc cgc cag       576
Val Ser Gly Leu Thr Phe Ser Arg Phe Trp Met Ser Trp Val Arg Gln
            180                 185                 190 tct cca gag aag ggg ctt gag tgg gtt gct gaa att aga ttg aaa tct       624
Ser Pro Glu Lys Gly Leu Glu Trp Val Ala Glu Ile Arg Leu Lys Ser
        195                 200                 205 gat aat tat gca aca cat tat gcg gag tct gtg aaa ggg aag ttc acc       672
Asp Asn Tyr Ala Thr His Tyr Ala Glu Ser Val Lys Gly Lys Phe Thr
    210                 215                 220 atc tca aga gat gat tcc aaa agt cgt ctc tac ctg caa atg aac agc       720
Ile Ser Arg Asp Asp Ser Lys Ser Arg Leu Tyr Leu Gln Met Asn Ser
225                 230                 235                 240 tta aga act gaa gac act gga att tat tac tgt aaa atc tat ttt tac       768
Leu Arg Thr Glu Asp Thr Gly Ile Tyr Tyr Cys Lys Ile Tyr Phe Tyr
                245                 250                 255 tct ttt tct tac tgg ggc caa ggg act ctg gtc act gtc tct gca gcc       816
Ser Phe Ser Tyr Trp Gly Gln Gly Thr Leu Val Thr Val Ser Ala Ala
            260                 265                 270
```

```
tcc aca cag agc cca tcc gtc act agt ggc cag gcc ggc c                    856
Ser Thr Gln Ser Pro Ser Val Thr Ser Gly Gln Ala Gly
        275                 280                 285
```

<210> SEQ ID NO: 4
<211> LENGTH: 285
<212> TYPE: PRT
<213> ORGANISM: Artificial Sequence
<220> FEATURE:
<223> OTHER INFORMATION: Description of Artificial Sequence: Nucleotide
      residue sequence of catalytic fragment

<400> SEQUENCE: 4

```
Ala Thr Val Ala Gln Ala Ala His His His His His Val Ala Gln
 1               5                  10                  15

Ala Ala Ser Ser Glu Leu Asp Val Val Met Thr Gln Thr Pro Leu Ser
            20                  25                  30

Leu Pro Val Ser Leu Gly Asp Gln Ala Ser Ile Ser Cys Arg Ser Ser
            35                  40                  45

Gln Ser Leu Val His Ser Tyr Gly Asn Thr Phe Leu Asn Trp Tyr Leu
50                  55                  60

Gln Lys Ser Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Leu Gly Val
            100                 105                 110

Tyr Phe Cys Ser Gln Gly Thr His Val Pro Tyr Thr Phe Gly Gly Gly
            115                 120                 125

Thr Lys Leu Glu Leu Lys Ser Gly Gly Gly Ser Gly Gly Gly
            130                 135                 140

Gly Gly Gly Ser Ser Arg Ser Ser Leu Glu Val Met Leu Val Glu Ser
145                 150                 155                 160

Gly Gly Gly Leu Val Gln Pro Gly Gly Ser Met Lys Leu Ser Cys Val
                165                 170                 175

Val Ser Gly Leu Thr Phe Ser Arg Phe Trp Met Ser Trp Val Arg Gln
                180                 185                 190

Ser Pro Glu Lys Gly Leu Glu Trp Val Ala Glu Ile Arg Leu Lys Ser
            195                 200                 205

Asp Asn Tyr Ala Thr His Tyr Ala Glu Ser Val Lys Gly Lys Phe Thr
210                 215                 220

Ile Ser Arg Asp Asp Ser Lys Ser Arg Leu Tyr Leu Gln Met Asn Ser
225                 230                 235                 240

Leu Arg Thr Glu Asp Thr Gly Ile Tyr Tyr Cys Lys Ile Tyr Phe Tyr
                245                 250                 255

Ser Phe Ser Tyr Trp Gly Gln Gly Thr Leu Val Thr Val Ser Ala Ala
            260                 265                 270

Ser Thr Gln Ser Pro Ser Val Thr Ser Gly Gln Ala Gly
            275                 280                 285
```

<210> SEQ ID NO: 5
<211> LENGTH: 899
<212> TYPE: DNA
<213> ORGANISM: Mus musculus

<400> SEQUENCE: 5

```
ttttaagaag cgtagtccgg aacgtcgtac gggtactggc cggcctggcc actagtgacg      60
```

| | |
|---|---|
| gatgggctct gtgtggaggc tgcagagaca gtgaccagag tccccttggcc ccagtaagaa | 120 |
| aatgagtaaa aataggtttt acagtaataa attccagtgt cttcagttct taagctgttc | 180 |
| atttgcaggt agagacgact tttggaatca tctcttgaga tggtgaactt ccctttcaca | 240 |
| gactccgcat aatgtgttgc ataattatca gatctcaatc taatttcagc aacccactca | 300 |
| agccccttct ctggagactg gcggacccaa gacatccaat aatttctgaa agttaatcca | 360 |
| gaaatttcac aggagagttt catggttcct ccaggttgca ccaagcctcc tccagactcc | 420 |
| accaacatca cctcgaggga agatctagag gaaccacccc caccaccgcc cgagccaccg | 480 |
| ccaccagagg attttatttc cagcttggtc cccctccga acgtgtacgg aagatgtgta | 540 |
| ccttgagagc agaaataaac tcccagatcc tcagcctcca ctttgctgat cctgagtgtg | 600 |
| aaatctgtcc ctgatccact gccactgaac ctgtctggga ccccagaaaa gcggttggaa | 660 |
| actttgtaga tcaggagctt tggcgactgg cctggcttct gcaggtacca atttaaatag | 720 |
| gggcttccat aagtgtgtag aaggctctga ctagatctgc aagagatgga ggcttgatct | 780 |
| ccaagacgga caggcaggga gagtggagac tgggtcatca caatgtcgag ctcggaactg | 840 |
| gccgcctggg ccacatggtg gtggtggtag tgagcagcct gagcaacggt agcgaaacc | 899 |

<210> SEQ ID NO: 6
<211> LENGTH: 856
<212> TYPE: DNA
<213> ORGANISM: Artificial Sequence
<220> FEATURE:
<223> OTHER INFORMATION: Description of Artificial Sequence: Nucleotide residue sequence of catalytic fragment.

<400> SEQUENCE: 6

| | |
|---|---|
| ggccggcctg gccactagtg acggatgggc tctgtgtgga ggctgcagag acagtgacca | 60 |
| gagtcccttg gccccagtaa gaaaaagagt aaaaatagat tttacagtaa taaattccag | 120 |
| tgtcttcagt tcttaagctg ttcatttgca ggtagagacg acttttggaa tcatctcttg | 180 |
| agatggtgaa cttcccttc acagactccg cataatgtgt tgcataatta tcagatttca | 240 |
| atctaatttc agcaacccac tcaagcccct ctctggaga ctggcggacc caagacatcc | 300 |
| agaatctact gaaggttaat ccagacacca cacaggagag tttcatggat cctccaggtt | 360 |
| gcaccaagcc tcctccagac tccaccagca tcacctcgag ggaagatcta gaggaaccac | 420 |
| ccccaccacc gcccgagcca ccgccaccag aggatttcag ctccagcttg gtccccctc | 480 |
| cgaacgtgta cggaacatgt gtaccttgag agcagaaata aactcccaga tcctcagcct | 540 |
| ccactctgct gatcttgagt gtgaaatctg tccctgatcc actgccactg aacctgtctg | 600 |
| ggaccccaga aaatcggttg gaactttgt agatcaggag ctttggagac tggcctgact | 660 |
| tctgcaggta ccaatttaaa aaggtgtttc cataactgtg tacaaggctc tgactagatc | 720 |
| tgcaagagat ggaggcttga ctccaagac tgacaggcag ggagagtgga gtctgggtca | 780 |
| tcacaacatc gagctcggaa ctggccgcct gggccacatg gtgatggtga tggtgagcag | 840 |
| cctgagcaac ggtagc | 856 |

What is claimed is:

1. A compound according to formula I, below

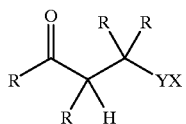

where X is a heteroatom of a therapeutic agent, Y is absent or a self-immolative linker and each R is independently hydrogen, $C_1$–$C_6$ alkyl, $C_1$–$C_6$ alkenyl, $C_5$–$C_6$ aryl or a heterocycle containing five or six ring atoms.

2. The compound of claim 1 wherein the self-immolative linker is

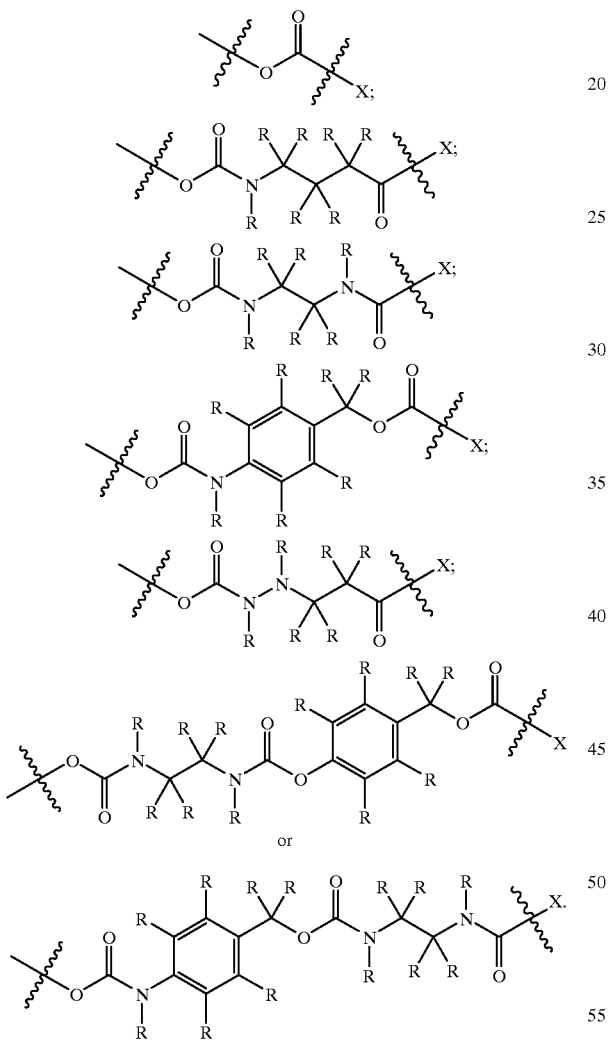

3. The compound of claim 1 wherein the heteroatom is a nitrogen, oxygen or sulfur atom in a functional group of the target molecule.

4. The compound of claim 1 wherein the therapeutic agent is an anti-tumor agent.

5. The compound of claim 4 wherein the anti-tumor agent is a cytotoxic agent.

6. The compound of claim 4 wherein the anti-tumor agent is an antibiotic.

7. The compound of claim 6 wherein the antibiotic is an anthracycline antibiotic.

8. The compound of claim 7 wherein the anthracycline antibiotic is doxorubicin or a therapeutically active analog thereof.

9. The compound of claim 6 wherein the anti-tumor agent is a microtubule stabilizing agent.

10. The compound of claim 9 wherein the microtubule stabilizing agent is paclitaxel, epothilone, or a therapeutically active analog thereof.

11. A compound having the structure, below

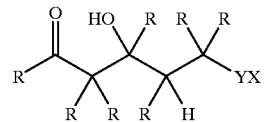

where X is a heteroatom of a therapeutic agent, Y is absent or a self-immolative linker and each R is independently hydrogen, $C_1$–$C_6$ alkyl, $C_1$–$C_6$ alkenyl $C_5$–$C_6$ aryl or a heterocycle containing five or six ring atoms.

12. A compound of the structure

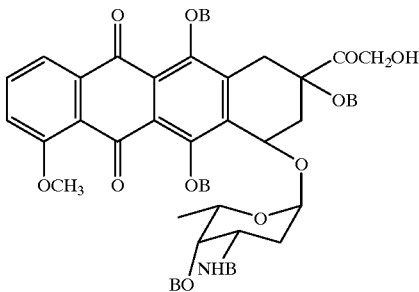

where each B is independently H,

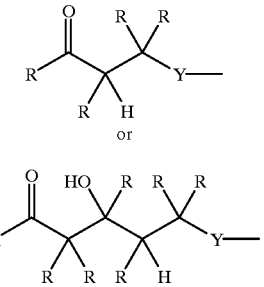

or

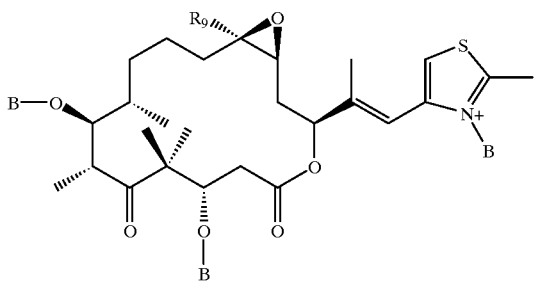

where Y and R are as defined in claim 1 and with the proviso that two Bs are H.

13. A compound of the structure

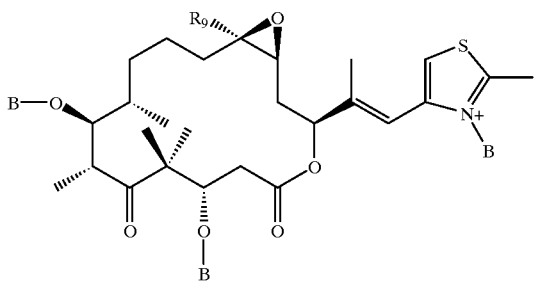

where $R^9$ is $CH_3$, $CH_2F$, $CH_2Cl$, $CH_2CH_3$, $CH_2OOCCH_3$ or $CH=CH_2$ and each B is independently H,

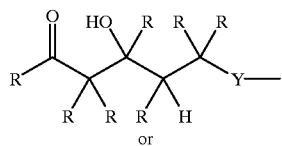

or

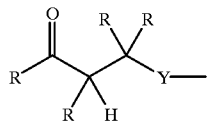

where Y and R are as defined in claim 1 and with the proviso that two Bs are H.

14. A compound according to formula I, below

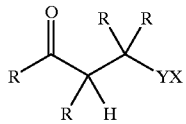
                         I where X is a heteroatom of a chromophore or fluorophore, Y is absent or a self-immolative linker and each R is independently hydrogen, $C_1$–$C_6$ alkyl, $C_1$–$C_6$ alkenyl, $C_5$–$C_6$ aryl or a heterocycle containing five or six ring atoms.

15. A compound having the structure, below

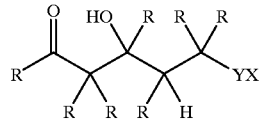

where X is a heteroatom of a chromophore or fluorophore, Y is absent or a self-immolative linker and each R is independently hydrogen, $C_1$–$C_6$ alkyl, $C_1$–$C_6$ alkenyl, $C_5$–$C_6$ aryl or a heterocycle containing five or six ring atoms.

* * * * *